(12) United States Patent
Sieber-Blum et al.

(10) Patent No.: US 8,030,072 B2
(45) Date of Patent: Oct. 4, 2011

(54) METHOD OF ISOLATING EPIDERMAL NEURAL CREST STEM CELLS

(75) Inventors: Maya Sieber-Blum, Brookfield, WI (US); Milos Grim, Prague (CZ)

(73) Assignees: Newcastle University, New Castle Upon Tyne (GB); Univerzita Karlova V Praze, Prague (CZ)

( * ) Notice: Subject to any disclaimer, the term of this patent is extended or adjusted under 35 U.S.C. 154(b) by 521 days.

(21) Appl. No.: 11/376,498

(22) Filed: Mar. 15, 2006

(65) Prior Publication Data

US 2006/0281177 A1    Dec. 14, 2006

Related U.S. Application Data

(60) Provisional application No. 60/661,973, filed on Mar. 15, 2005.

(51) Int. Cl.
*C12N 5/071* (2010.01)
(52) U.S. Cl. .................. 435/368; 435/378; 435/366
(58) Field of Classification Search .............. 435/368, 435/378, 366
See application file for complete search history.

(56) References Cited

FOREIGN PATENT DOCUMENTS

WO    WO 03/054202 A1 * 7/2008

OTHER PUBLICATIONS

Muller et al. Nat. Reviews, 7: 75-84, 2006.*
Ferletta. Mol. Can. Res., 5(9): 891-897, 2007.*
Xu et al. J. of Cell Bio., 154(1): 217-229, 2001.*
Kim et al. (Production of Immortalized Human Neural Crest Stem Cells, from Meth. Mol. Bio., 198: 55-65, 2002.*
Xu et al. J. of Cell Bio., 154(1): 217-229, 2001.*
Rao. J. Neurobiol., 32: 722-746, 1997.*
Sieber-Blum. Stem Cell Rev., 4:256-260, 2008.*

Claudinot, S., et al., "Long-term renewal of hair follicles from clonogenic multipotent stem cells," PNAS 102:14677-14682 (2005).
Fernandes, K.J., et al., "A dermal niche for multipotent adult skin-derived precursor cells," Nature Cell Biology 6:11:1082-1093 (2004).
Ito, M., et al., "Stem cells in the hair follicle bulge contribute to wound repair but not to homeostasis of the epidermis," Nature Medicine 11:12:1351-1354 (2005).
Kruger, G.M., et al., "Neural Crest Stem Cells Persist in the Adult Gut but Undergo Changes in Self-Renewal, Neuronal Subtype Potential . . . ," Neuron 35:657-669 (2002).
Li, L., et al., "Nestin expression in hair follicle sheath progenitor cells," PNAS 100:17:9958-9961 (2003).
Sieber-Blum, M., et al., "Pluripotent Neural Crest Stem Cells in the Adult Fair Follicle," Developmental Dynamics 231:258-269 (2004).
Sieber-Blum, M., et al., "The Adult Hair Follicle: Cradle for Pluripotent Neural Crest Stem Cells," Birth Defects Research 72:163-172 (2004).
Sieber-Blum, M., et al, "Neural Crest Stem Cells in the Adult Mammalian Epidermis," Faseby 18:4:Part I Abstract p. A25 (2004).
Toma, J.G., et al., "Isolation of multipotent adult stem cells from the dermis of mammalian skin," Nature Cell Biology 3:778-784 (2001).
Hu, Y.F., et al.,"An Epidermal Neural Crest Stem Cell (EPI-NCSC) Molecular Signature," Stem Cells 24:2692-2702 (2006).
Sieber-Blum, M., et al., "Characterization of Epidermal Neural Crest Stem Cell (EPI-NCSC) Grafts in the Lesioned Spinal Cord," Mol. Cell. Neurosci. 32:67-81 (2006).
Thomas et al., Human neural crest cells display molecular and phenotypic hallmarks of stem cells, Human Molecular Genetics 17: 3411-3425, 2008.
Thomas et al., Human neural crest cells display molecular and phenotypic hallmarks of stem cells; Supplementary Table 8, Human Molecular Genetics 17: 3411-3425, 2008.

* cited by examiner

*Primary Examiner* — Thaian N Ton
(74) *Attorney, Agent, or Firm* — Quarles & Brady LLP; Sara D. Vinarov

(57) ABSTRACT

The present invention describes novel methods for isolating a substantially pure cell population of non-embryonic epidermal neural crest stem cells from the bulge-region of mammalian hair follicles. Also disclosed is the substantially pure cell population of follicular bulge-derived neural crest stem cells for medical research and therapeutic use.

16 Claims, 20 Drawing Sheets

A  B

A  B

A
B

A B

METHOD OF ISOLATING EPIDERMAL NEURAL CREST STEM CELLS

CROSS-REFERENCE TO RELATED APPLICATIONS

This application claims the benefit of U.S. Provisional Application No. 60/661,973 filed Mar. 15, 2005. This application is incorporated herein by reference in its entirety.

STATEMENT REGARDING FEDERALLY SPONSORED RESEARCH OR DEVELOPMENT

This invention was made with United States government support awarded by National Institute of Neurological Disorders and Stroke, NIH; USPHS grant NS38500. The United States government has certain rights in this invention.

BACKGROUND OF THE INVENTION

The neural crest is a transient tissue of the vertebrate embryo that originates in the neural folds, invades the embryo, and differentiates in distinct locations into a wide array of adult cell types and tissues. Neural crest derivatives include neurons, Schwann cells, and glia of the autonomic and enteric nervous systems, most primary sensory neurons, endocrine cells (e.g., the adrenal medulla and C-cells of the thyroid), the smooth musculature of the cardiac outflow tract and great vessels, pigment cells of the skin and internal organs, tooth papillae, meninges, as well as bone, cartilage, and connective tissue (dermis) of the face, forehead and ventral part of the neck (LeDouarin and Kalcheim, *The Neural Crest*, Cambridge University Press, 1999).

Recently, Anderson et al. reported methods for the isolation and clonal propagation of mammalian neural crest stem cells. Their methods use a separation and culturing regimen and bioassays for establishing the generation of neural crest stem cell derivatives. In their method, the neural crest stem cells are cultured on a mixed substrate of poly-D-lysine and fibronectin to generate neurons and glia. The cells were also found to express low-affinity nerve growth factor receptor (LNGFR) and nestin, but do not express glial fibrillary acidic protein (GFAP) (See U.S. Pat. No. 5,589,376). One of the problems with this method is that the cells originate from the embryonic neural tube. The procedure raises ethical considerations, as several week old embryos would be destroyed during isolation of embryonic neural crest cells. Ethical issues aside, the method from a practical standpoint is not feasible, as it is unlikely to provide a sufficient amount of neural tissue to meet the demands of therapeutic procedures, such as transplantation for cell replacement therapy. Thus, this cell source is not particularly desirable for transplantation.

Alternatively, Miller et al. reported the isolation of multipotent neural stem cells (MNSCs) from the peripheral tissue of postnatal mammals, including juvenile and adult mammals. They identified skin as a source of MNSCs and set forth methods to purify skin-derived MNSCs, thus simplifying the harvesting of cells for transplantation relative to previous methods (See U.S. Pat. No. 6,787,355). However, this population of cells is still fairly heterogenous (i.e., at least 30% of the cells are multipotent stem cells), requiring a series of additional purification steps to become useful for human medical procedures. In particular, MNSCs require multiple sub-cultures over a period of several weeks during which time their stem cell characteristics could change through, for example, the action of autocrine or paracrine differentiation factors due to the close proximity of cells. Furthermore, the ontological source of the MNSCs is unclear.

Accordingly, it would be useful to have a method for producing a substantially homogenous population of neural crest stem cells from a readily accessible source for medical research and therapeutic purposes.

BRIEF SUMMARY OF THE INVENTION

The present invention is summarized as providing methods for producing a substantially pure and expanded population of non-embryonic neural crest stem cells from mammalian hair follicles. The method includes providing epidermal tissue with hair follicles from a mammal and dissecting the hair follicles by removing dermis, connective tissue and fat cells; and isolating the bulge region of the hair follicles. The bulge regions are then cultured as adherent explants on collagen-, and fibronectin-coated culture substrates to isolate the epidermal neural crest stem cells (EPI-NCSCs, previously referred to as eNCSCs). EPI-NCSCs emigrate from the bulge explants onto the collagen/fibronectin substratum and are then cultured first as primary explants and then sub-cultured as adherent cells under suitable conditions to produce a substantially pure population of EPI-NCSCs, which can be readily expanded in subculture.

In this aspect, the culture conditions include alpha-modified MEM culture medium, ITS+3 (insulin, transferring, selenium plus 3 essential fatty acids), chick embryo extract, and members of the following families of growth factors: fibroblast growth factors, epidermal growth factors and neurotrophins.

In this aspect, the EPI-NCSCs are multipotent and capable of differentiating into all major neural crest derivatives, including neurons, Schwann cells, smooth muscle cells, cartilage/bone cells and melanocytes.

In this aspect, the non-embryonic EPI-NCSCs may be found in epidermal tissue from adults, juveniles, or newborns. In this aspect, the cell population is characterized by the positive expression of Sox-10, Nestin, and marker genes including Pcbp4 (Mm.286394), Msx2 (Mm.1763), H1fx (Mm.33796), Thop1 (Mm.26995), Vars2 (Mm.28420), Myo10 (Mm.60590), 2700094K13Rik (Mm.259293), Ets1 (Mm.292415), Pygo2 (Mm.22521) Adam12 (Mm.323601) 5730449L18Rik (Mm.21065), Rex3 (Mm.14768), Vdac1 (Mm.3555), AU041707 (Mm.200898), Pfn1 (Mm.2647), Crmp1 (Mm.290995), Ube4b (Mm.288924) and combinations thereof.

In this aspect, at the onset of primary explant culture the cell population has a purity level of greater than 70% and preferably at least 83% multipotent stem cells without any need to further purify the cells.

In this aspect the cells adhere to a substratum comprised of collagen, and fibronectin.

Also, described is a substantially pure population of multipotent mammalian non-embryonic neural crest stem cells comprising cells which (i) are derived from the epidermal bulge region of a hair follicle, (ii) have a purity level of greater than 70% epidermal neural crest stem cells at the onset of emigration from the hair follicle, (iii) are multipotent, (iv) capable of undergoing differentiation to give rise to all major neural crest derivatives, (v) are highly proliferative in in vitro culture, (vi) are highly motile, (vii) exhibit a high degree of plasticity, (viii) are characterized by the positive expression of Sox-10, Nestin, and the panel of markers termed 'a neural crest stem cell molecular signature' listed in Table 1 (ix) are stellate shape in morphology, (x) are characterized by the absence of expression of the hematopiotetic and keratinocyte stem cell marker, CD34, and by the absence of the MNSC marker, alkaline phosphatase.

In one aspect, the population is composed of greater than 83% multipotent epidermal neural crest stem cells at the onset of emigration from the hair follicle without any need to further purify the cells.

An important feature of the novel EPI-NCSC population is that it provides a non-controversial substitute for embryonic stem cells.

Another advantage of EPI-NCSC is their high degree of innate plasticity, in the sense that similar to embryonic stem cells, EPI-NCSC are physiologically predestined to give rise the many different cell types, including neurons, nerve supporting cells, smooth muscle cells, cartilage/bone cells and melanocytes.

Another advantage of the EPI-NCSCs is that they are highly accessible using minimally invasive procedures.

Another advantage of EPI-NCSCs is that they can be used for autologous transplantation, preventing graft-rejection.

Other objects, features, and advantages of the present invention will become obvious after study of the specification, drawings, and claims.

DETAILED DESCRIPTION OF THE INVENTION

Figure 1:
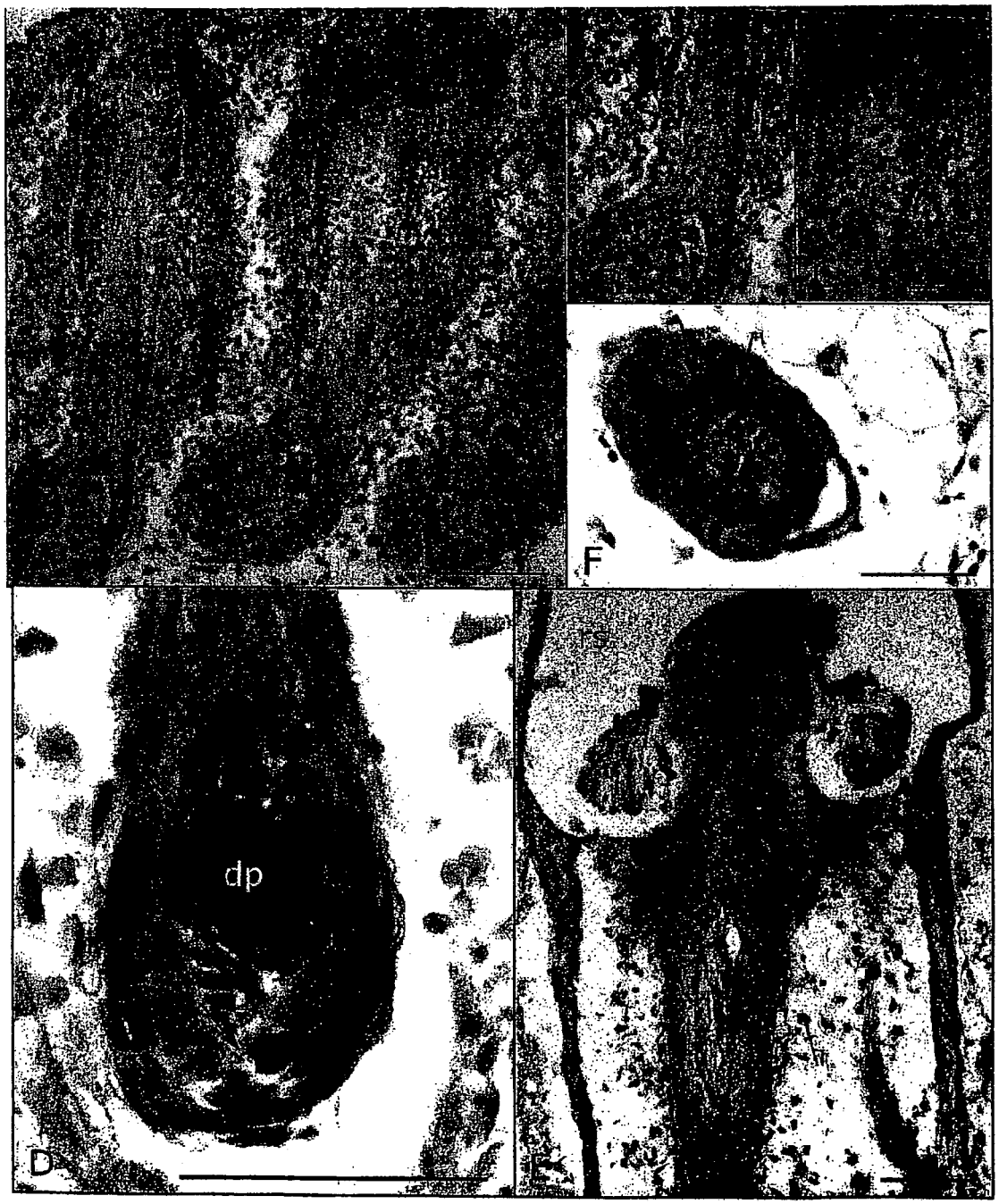
FIG. 1 shows X-gal-positive cells in the Wnt1-cre/R26R prenatal and postnatal mouse whisker follicle. In Wnt1-cre/R26R double transgenic mice, neural crest cells are specifically and permanently marked by their expression of beta-galactosidase. Beta-galactosidase can be visualized histochemically as a blue reaction product. (A) Tangential section through whiskers of a gestational day 16.5 mouse embryo. Xgal-positive neural crest-derived cells are present in the dermis (d) between whiskers, in the dermal papilla (dp), and in the blood sinuses (bs) that surround the whiskers. In addition, neural crest cells are localized in the outer root sheath within the follicle. (B) Higher magnification of the area marked at the left in (A). A stream of neural crest cells extends from the bulge region to the matrix near the dermal papilla (arrows), suggesting migratory behavior within the follicle. (C) Higher magnification of area marked at the right in (A). This section shows the bulge area. Many neural crest cells are present (e.g., arrow). (D) Section through the base of a whisker follicle of a newborn double transgenic mouse. Several Xgal-positive melanoycte are visible (e.g. arrows). (E) Tangential section through postnatal day 24 whisker follicle. The bulge region (b) contains several Xgal-positive neural crest cells (e.g., arrow). The hair is marked by an asterisk. rs; ring sinus. (F) Cross section through a whisker from an adult double transgenic mouse at the level of the dermal papilla (dp). Several neural crest-derived Xgal-positive cells (e.g. arrows) are present in the matrix, which surrounds the dermal papilla. Bars, (A), 100 µm; (B, C), 50 µm, (D), 50 µm, (E), 100 µm, (F) 50 µm. (Note: Blue, Xgal reaction product; red, nuclear red counter-stain.)

The various embodiments of the present invention described herein are premised on our recent observation, isolation, expansion, and characterization of a substantially pure EPI-NCSC population derived from the bulge-region of the non-embryonic mammalian hair follicles.

Accordingly, in one embodiment, the present invention relates to novel methods for isolating and expanding in vitro a substantially pure population of non-embryonic mammalian epidermal neural crest stem cells (EPI-NCSCs) from hair follicles. In another embodiment, the present invention relates to a novel population of EPI-NCSCs isolated by the methods described herein. These embodiments of the invention are premised on our recent observation, isolation, expansion, and characterization of a substantially pure EPI-NCSC population derived from the bulge-region of the non-embryonic mammalian hair follicles.

In a preferred embodiment, the method includes providing epidermal tissue with hair follicles from a mammal; dissecting the hair follicles by removing dermis, connective tissue and fat cells; and isolating the bulge regions of the hair follicles. The bulge regions are then cultured as adherent explants on collagen coated culture substrates to isolate the epidermal neural crest stem cells (EPI-NCSCs, previously referred to as eNCSCs). The isolated EPI-NCSCs are then cultured as primary explants for 6-8 days and then sub-cultured as adherent cells at $1\times10^4$ cells per 35 mm culture culture plate (pre-coated with collagen and fibronectin) under suitable conditions (85% Alpha-modified MEM medium supplemented with 5% chick embryo extract and 10% fetal bovine serum) to produce a substantially pure population of EPI-NCSCs, which can be readily expanded by subculture.

In this embodiment, the bulge regions of the mammalian hair follicles are cultured on adherent explants are cultured on extra cellular matrix-coated culture substrates, wherein the substratum is composed of collagen and fibronectin.

In one embodiment of the disclosed method, the culture includes alpha-modified MEM culture medium, ITS+3, chick embryo extract, and members of the following families of growth factors: fibroblast growth factors, epidermal growth factors, stem cell factor, neurotrophins.

In another embodiment, the isolation of the EPI-NCSCs from mammalian hair follicles yields at least $2.2\times10^3$ cells per explant, within 3-4 days after the onset of emigration from the bulge explant in primary culture. The isolation of the EPI-NCSCs from mammalian hair follicles is equal or greater than 24× expansion in secondary culture, which equals 52, 800 cells per explant within 11-12 days. This is typically 3-4 days as primary explant plus 8 days in subculture. Moreover, the isolation of the EPI-NCSCs from mammalian (e.g., mouse) hair follicles is equal or greater than 844,800 cells per mouse within 14-16 days. This is typically 3-4 days in primary explant culture before onset of emigration of cells, plus 3-4 days after the onset of cell emigration and 8 days in subculture.

An advantage of this embodiment is that the isolated EPI-NCSC population is substantially pure. The term "substantially pure", as used herein means that at the onset of emigration from the hair follicle, the isolated cell population of neural crest cells includes greater than 70% and preferably at least 83% and more preferably 90% multipotent neural crest stem cells. In other words, the term "substantially pure" refers to a population of progenitor cells that contain fewer than about 30%, more preferably fewer than about 17%, most preferably fewer than about 10% of lineage committed cells in the original expansion and isolated population prior to subsequent culturing and expansion. This high level of purity is obtained by following the methods set forth herein without any need for additional purification steps to further purify the cells. Thus, the method described herein provides an efficient, time saving process for producing a substantially pure population of EPI-NCSCs for therapeutic purposes.

As used herein the term "EPI-NCSC" refers to those cells that originate from the neural folds of the neuroepithelium and reside in the epidermal bulge region of non-embryonic hair follicle. Soon after emigration from the embryonic neural tube (in the mouse embryo at gestational day 9.5 or earlier; Sieber-Blum et al., 2004), EPI-NCSCs invade the somatic ectoderm and become located in the bulge of hair follicles.

As used herein the term "non-embryonic" stem cells refers to adult, juvenile or newborn stem cells. No one was harmed in the process. No embryos or unborn are involved in the collection of the cells or their transplantation. Further, they are an undifferentiated cell found in a differentiated tissue (e.g., epidermis) that can renew itself and (with certain limitations) differentiate to yield all the specialized cell types of the tissue from which it originated.

As used herein, the "neural crest" is a transient embryonic tissue (a band of cells that extend lengthwise along the neural tube of an embryo) that contains highly plastic multipotent stem cells, which are capable of undergoing self-renewal and give rise to cells that form the cranial, spinal, autonomic and enteric ganglia, as well as becoming odontoblasts, which form the calcified part of the teeth, as well as many other cell types and tissues.

As used herein the term "neural crest derivatives" include the autonomic nervous system (sympathetic and parasympathetic), the enteric nervous system, most primary sensory neurons, smooth muscle cells of the cardiac outflow tract and great vessels of the head and neck, endocrine cells (adrenal medulla, calcitonin-producing-cells of the thyroid), pigment cells of the skin and internal organs, and the following craniofacial structures: connective tissue, cartilage and bone of the face, forehead and ventral neck, tooth papillae, meninges, striated muscle of the eye and the stromal cells of the cornea. Under conducive culture conditions described herein EPI- NCSCs can differentiate into all major neural crest derivatives, including neurons, Schwann cells, cartilage cells, bone cells, myofibroblasts and pigment cells. This observation indicates the EPI-NCSC can express all major neural crest derivatives.

As used herein the term "multipotent" refers to stem cells that have the capability of developing cells of multiple germ layers, particularly cells described herein.

As used herein the term "plastic" or "plasticity" refers to the ability of stem cells from one adult tissue to generate two or more differentiated types of progeny. Also, the phrase "high degree of physiological plasticity" refers to the fact that neural crest cells are capable of generating a wider range of cell types that are typical for ectodermal derivatives (e.g., neurons, Schwann cells, corneal stroma, meninges, pigment cells, endocrine cells), and mesodermal derivatives (e.g., cartilage, bone, tooth papillae, myofibroblast, connective tissue) in relative to other stem cells of non-embryonic origin.

Indeed, it is believed that the neural crest contributes to the body organs and tissues, ranking it with the ectoderm, mesoderm, and endoderm as a fourth germ layer (Hall B K. 2000. The neural crest as a fourth germ layer and vertebrates as quadroblastic not triploblastic. *Evol Dev* 2: 3-5). Neural crest cells are capable of generating neurons, Schwann cells, pigment cells, endocrine cells, odontoblasts, fibroblasts, osteoblasts, chondroblasts, and myofibroblasts.

As used herein the term "explant" refers to a portion of an organ (i.e., epidermis) taken from the body and grown in an artificial medium.

As used herein the phrase "adherent explants" refers to bulge regions that have been explanted to empty collagen-coated culture plates, preincubated with culture medium for 1-3 hours. Under these conditions the bulge regions adhere to the collagen substratum within one hour, at which time the culture medium described herein is added.

As used herein the phrase "adherent cells" refers to cells that are cultured while adhering to a collagen substratum in either tissue culture plastic plates, flasks, or on microcarriers.

As used herein the phrase "highly proliferative in in vitro culture" refers to the fact that the cells have a population doubling time that initially in primary explants is approximately six hours, and later in expansion culture approximately 28 hours.

Figure 5:
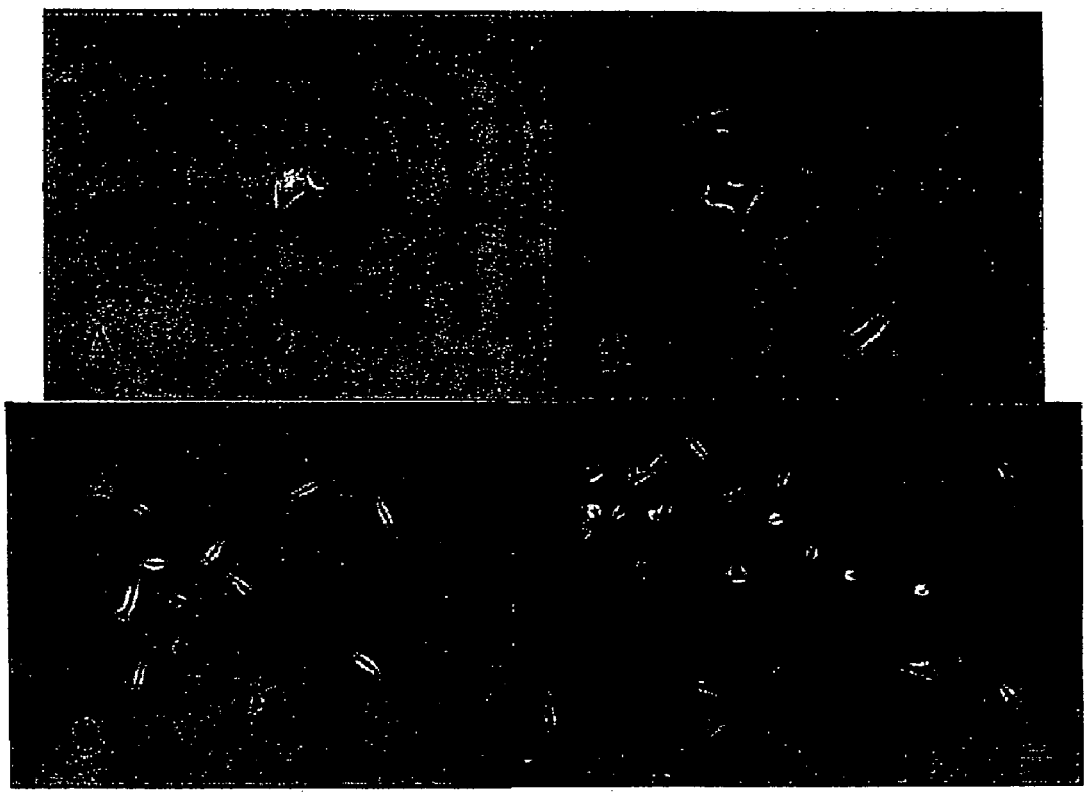
FIG. 5 shows a bulge-derived cells in clonal culture. (A) One cell 6 hours after cloning. (B) Four daughter cells from the same clone-forming cell as in (A) at 18 hours. (C) The same clone at 48 hours consists of approximately 13 cells. (D) The same clone at 72 hours. The changing shape of the clone reflects the high motility of the cells. Bars, (A, B) 50 µm; (C, D), 50 µm.
Figure 16:
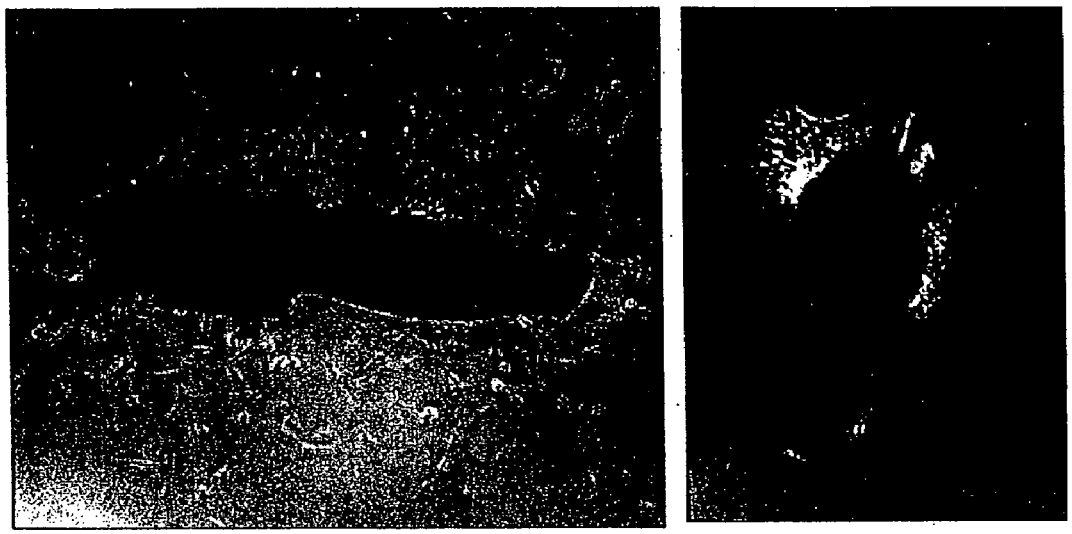
FIG. 16 shows human hair in culture 4 days after explantation. Dissected hair was cut into 3 pieces and placed into collagen-coated culture plates. Cells emigrated from many explants. (A) Most cells had the morphology of neural crest cells. (B) Rare explants released keratinocyte cells (or keratinocyte stem cells, also termed 'epidermal stem cells'), which are easily distinguished from neural crest-like cells because they are less motile and have a cobble-stone morphology. Our current results show that neural crest-like cells can be isolated from human hair follicles at least up to 5 days postmortem.

As used herein the phrase "highly motile" refers to the fact that the cells emigrate from the bulge explants as illustrated in FIG. 3A and translocate randomly in the culture plate as illustrated in FIG. 5 for clonal cultures, whereas epidermal stem cells remain near the explant (FIG. 16B).

As used herein the phrase "at the onset of emigration from the hair follicle" refers to the point in time at which the first EPI-NCSCs emerge from the bulge explants, usually 2-4 days post-explantation.

As used herein, the "bulge region" is a defined, compact area in the mouse whisker follicle. It also exists in hair follicles of other parts of a mammal. The bulge region is more elongated in human hair follicles.

The term "culture substrates" as used herein refers to any surface that can be used for effectively isolating and culturing the EPI-NCSCs. These can include for example, collagen-coated tissue culture Petri dishes, culture flasks, and the Nunc Cell Factory, which are all effective at culturing small quantities of attachment dependent cells. It also refers to microcarriers, fiber beds, hollow fiber cartridges and stacked plate modules used for attachment dependent cell culture scale up. For example, microcarriers are tiny beads or particles with a surface chemistry that facilitates attachment and growth of anchorage-dependent cells in cell culture processes for scale-up purposes. There are numerous types of microcarriers, widely varying in their composition, size, shape and density including but not limited to HyQ® Spheres™ Microcarriers, PuraMatrix™ Peptide Hydrogels, and others.

In a preferred embodiment of the substantially pure population of multipotent mammalian non-embryonic EPI-NCSC, the cells (i) are derived from the epidermal bulge region of a hair follicle, (ii) have a purity level of greater than 70% and typically 83% EPI-NCSCs at the onset of emigration from the hair follicle, (iii) are multipotent, (iv) capable of undergoing directed differentiation to give rise to neural crest cells, (v) are highly proliferative in vitro culture, (vi) are highly motile, (vii) exhibit a high degree of plasticity, (viii) are stellate shape in morphology, and (ix) are characterized by the positive expression of Sox-10, Nestin (an intermediate filament protein found in cells such as neural precursors) and the expressed neural crest stem cell signature marker genes, listed in Table 1.

TABLE 1

List of genes comprising the neural crest stem cell molecular signature.

| Gene name | Unigene number |
|---|---|
| Pcbp4 | Mm.286394 |
| Msx2 | Mm.1763 |
| H1fx | Mm.33796 |
| Thop1 | Mm.26995 |
| Vars2 | Mm.28420 |
| Myo10 | Mm.60590 |
| 2700094K13Rik | Mm.259293 |
| Ets1 | Mm.292415 |
| Pygo2 | Mm.22521 |
| Adam12 | Mm.323601 |
| 5730449L18Rik | Mm.21065 |
| Rex3 | Mm.14768 |
| Vdac1 | Mm.3555 |
| AU041707 | Mm.200898 |
| Pfn1 | Mm.2647 |
| Crmp1 | Mm.290995 |
| Ube4b | Mm.288924 |

The marker genes were identified by long serial analysis of gene expression (LongSAGE). The rationale for creating a molecular signature is that a cell type cannot be identified adequately by a single marker gene, or a few marker genes, but by a panel of abundantly expressed marker genes only. Neural crest stem cell signature genes are defined according to the following stringent criteria: The genes (1) are significantly (>2-fold and p<0.05) more abundant in embryonic neural crest stem cell (NCSC) than in differentiated neural crest progeny (NCP), (2) are equivalently abundant in EPI-NCSC (p>0.07), and (3) are not expressed in bulge epidermal stem cells. Bulge neural crest stem cells were characterized by Tumbar et al. (2004), Defining the epithelial stem cell niche in skin. *Science.* 303:359-63.

Furthermore, there are several advantages to employing a substantially pure (homogenous) population of EPI-NCSCs from adults rather than the embryonic form. For example, similar to embryonic stem cells, the adult cells have the innate physiological ability to differentiate into many diverse cell types as indicated above. Another unique feature of EPI-NCSCs is their innate high degree of plasticity. Specifically, the high degree of plasticity exhibited by EPI-NCSCs allows them to differentiate into a wide array of cell types under physiological conditions.

Furthermore, EPI-NCSCs are easily accessible in the skin. More importantly, for cell therapy applications, an individual's own epidermal neural crest stem cells could be employed. This avoids rejection of the implant. These characteristics make EPI-NCSCs attractive candidates for diverse applications in cell replacement therapy.

Accordingly, it is envisioned that the substantially pure population of EPI-NCSCs isolated from adult hair follicles could be used in cell replacement therapy. Specifically, human EPI-NCSCs could be used in treating the following conditions and diseases: spinal cord injury, stroke, multiple sclerosis, tissue engineering of heart valves, cardiac birth defects, myocardial infarction, multiple sclerosis, Parkinson's disease, Hirschsprung's disease, Alzheimer's disease, craniofacial malformations/injuries, bone degeneration/bone fracture, neurofibromas in neurofibromatosis, peripheral neuropathies, and skin pigmentation defects. The cells could also be used for the regeneration of tooth papillae, adrenal medulla cells, and of calcitonin-producing cells of the thyroid.

The following examples provide the experimental materials and methods used to obtain and analyze the substantially pure population of EPI-NCSCs derived from the bulge region of mammalian hair follicles. These examples are intended to illustrate, but not limit, the present invention.

EXAMPLES

Example 1

Neural Crest-Derived Cells in Hair of Adult Mouse Whiskers

In this example, we demonstrate that the claimed method can be used to isolate multipotent neural crest stem cells from adult mammalian hair follicles. The following are experimental procedures used in isolating and characterizing a substantially pure population of EPI-NCSCs from bulge region of mouse whiskers as described in Sieber-Blum, M. et al, (2004) Pluripotent Neural Crest Stem Cells in the Adult Hair Follicle, *Developmental Dynamics* 231:258-269, incorporated by reference here in its entirety. The methods described herein can readily be adapted by one skilled in the art to isolate substantially pure populations of EPI-NCSCs from the hair follicles of other mammals.

Animals and Genotyping

Heterozygous Wnt1-cre mice were mated with R26R heterozygotes. Genotyping was performed exactly as described (Szeder, V., Grim, M., Halata, Z., and Sieber-Blum, M. (2003) Dev. Biol. 253: 258-263, incorporated by reference here in its entirety).

Bulge Explants

Whiskers were dissected from the whisker pad of four weeks to six months-old Wnt1-cre/R26R double transgenic mice according to a modified procedure of Baumann et al., (1996) An isolated rat vibrissal preparation with stable responses of slowly adapting mechanoreceptors. Neurosci. Lett. 26: 1-4, incorporated by reference herein in its entirety. The connective tissue was scraped from the follicle with a bent electrolytically sharpened tungsten needle and rinsed several times, thus exposing the ring sinus and cavernous sinus (FIG. 1B). The capsule was then cut longitudinally with a small scalpel, the blood flushed with a stream of Hanks' balanced salt solution, the follicle cross-sectioned first at the level above the cavernous sinus and then below the skin, yielding the bulge region within the capsule (FIG. 1C). The bulge was rolled out of the capsule, rinsed three times and plated in an empty collagen-coated 35-mm culture plate that had been pre-incubated for 3 hours with culture medium described below. The bulge explants adhered to the substratum within one hour, at which time 1.5 ml of culture medium was added.

The culture medium was designed to accommodate the survival and proliferation of neural crest stem cells, as well as their differentiation into multiple phenotypes, including neurons, smooth muscle cells, glia, chondrocytes and melanocytes (Ito, K., Morita, T. and Sieber-Blum, M. 1993. In vitro clonal analysis of mouse neural crest development. Dev. Biol. 157: 517-525; and Sieber-Blum, M. The neural crest colony assay: assessing molecular influences on development in culture. The Neuron in Tissue Culture (L. W. Haynes, ed.) IBRO, John Wiley & Sons Ltd. (1999) pp. 5-22; both are incorporated by reference here in their entirety). It consisted of 75% alpha-modified MEM medium, 5% day 11 chick embryo extract and 10% of fetal calf serum (HyClone), and it was supplemented with 1 μg/ml gentamycin as described previously (Sieber-Blum, 1999). Fifty percent of the culture medium was exchanged every other day.

Clonal Cultures

Cells started to emigrate from explants 48-72 hours post-explantation. At 4 days after onset of cell emigration, the bulge explant was removed, leaving the emigrated cells on the collagen substratum. The emigrated cells were then re-suspended by trypsin digestion exactly as described for mouse embryonic neural crest cells (Sieber-Blum, 1999). The percentage of single cells was 100, due to the sparse arrangement within early primary explants (FIG. 3A, C, E). Cells were plated at 20 cells per cm$^2$, which at a plating efficiency of approximately 10% yielded 8-10 clones per 35 mm culture plate. The cells adhered within 30 min. One hour after plating, single cells were marked by circling the underside of the plate with a diamond marker (4 mm diameter circle). Circles containing more than one cell were excluded from further evaluation. Fifty percent of the culture medium was exchanged every other day.

Subclones were prepared by removing the culture medium and placing a glass cloning ring around the clone. The clones within the rings were then rinsed with PBS and subsequently detached by trypsinization as described for primary explants. The clonal cell suspension consisting of 20-50 cells was subsequently placed into a new 35 mm culture dish.

Xgal Reaction and Indirect Immunocytochemistry

Cultures were fixed with 4% paraformaldehyde for 5 min at room temperature and Xgal histochemistry performed according to Galileo et al. (1990) with the modification that potassium ferricyanide and potassium ferrocyanide were used at 5 mM and incubation was overnight at 30° C. Subsequently the cultures were processed for indirect immunocytochemistry as follows. Cells were post-fixed with 4% paraformaldehyde for 30 min on ice, rinsed 3×10 min with PBS, blocked with 2% normal goat serum for 20 min and then incubated with pooled primary antibodies overnight in the cold. Subsequently, the plates were rinsed 3×10 min with PBS, incubated with pooled secondary antibodies for 2 hours at room temperature, rinsed 4×20 min with PBS, stained with DAPI nuclear stain (3 μM; Molecular Probes, Eugene Oreg.), rinsed again and finally mounted with ProLong Antifade (Molecular Probes, Eugene Oreg.) and a coverslip. The following primary antibodies were used: mouse monoclonal antibody against smooth muscle actin (1:800; Sigma, St. Louis Mo.); mouse monoclonal antibody against neuron-specific beta-III tubulin (1:200; Chemicon, Temecula Calif.); polyclonal rabbit anti-beta-III tubulin antibodies (1:400; Lee et al., 1990) rabbit polyclonal antibodies against S100 protein (1:200; Novocastra Laboratories, Newcastle upon Tyne UK); rabbit anti SCIP-antibodies (1:300; Zorick et al., 1996);

MelEM (melanocyte marker; 1:1; Hybridoma Bank; Nataf et al., 1993); Anti-Sox10 rabbit serum (1:100; Chemicon), Nestin mouse monoclonal antibodies (1:400; BD Biosciences); and mouse anti-GFAP ascites fluid (1:500; Chemicon). The following secondary antibodies were used at a dilution of 1:200; Texas red-conjugated and fluorescein-conjugated goat-anti-mouse IgG and goat anti-rabbit IgG designated for multiple labeling (Jackson ImmunoResearch, West Grove Pa.). The Xgal reaction in tissue sections was performed exactly as described (Szeder et al., 2003).

RT-PCR

Using Trizol reagent (Invitrogen), total RNA was prepared from cells that were grown for two weeks either in the presence of neuregulin1 (10 nM; for Schwann cell markers) or in its absence (for neuronal markers). Reverse transcription was performed with 3 μg of total RNA using SuperScript II reverse transcriptase (Invitrogen). PCR amplification was carried out with 50 ng of reverse transcribed DNA template, 10 pmol primers, and 0.2 mM dNTP. The PCR reaction consisted of denaturation at 94° C. for 45 s, annealing for 45 s (temperature dependent on the primer pair), and extension at 72° C. for 1 min. Annealing temperatures were as follows: P0, 59° C.; MAP2 and GFAP, 58° C.; beta-III tubulin and peripherin, 55° C.; /SCIP/Oct6, 52° C. PCR products were electrophoresed on 2% agarose gels and stained with ethidium bromide. The following primers were used: Protein zero (P0): forward, 5'-ACTATGCCAAGGGACAACCTTACATC-3', (SEQ ID NO:1); reverse, 5'-ACATAGAGCGTGACCT-GAGAGGTC-3', (SEQ ID NO:2); product size, 196 bp. Microtubule associated protein (MAP2): forward, GGC-CCAAGCTAAAGTTGG-3', (SEQ ID NO:3); reverse, 5'-CAAGCCAGACCTCACAGCG-3', (SEQ ID NO:4); product size, 215 bp. Neuron-specific beta-III tubulin: forward, 5'-CCCGTGGGCTCAAAATGT-3', (SEQ ID NO:5); reverse, 5'-TGGGGGCAGTGTCAGTAGC-3', (SEQ ID NO:6); product size, 380 bp. SCIP/Oct6: forward, 5'-AA-GAACATGTGCAAGCTCAA-3', (SEQ ID NO:7); reverse, 5'-ACAACAAAAAGAGTCCAGGC-3', (SEQ ID NO:8); product size 528 bp. Glial fibrillary acidic protein (GFAP); forward, 5'-CAAGCCAGACCTCACAGCG-3', (SEQ ID NO:9); reverse, 5'-GGTGTCCAGGCTGGTTTCTC-3', (SEQ ID NO:10); product size 508 bp. Peripherin; forward, 5'-ACAGCTGAAGGAAGAGATGG-3', (SEQ ID NO:11); reverse, 5'-GATTTGCTGTCCTGGGTATC-3', (SEQ ID NO:12); product size 538 bp. The RT-PCR products were sequenced for verification.

Results and Discussion

Using the experimental procedures described herein above, we identified the presence of multipotent neural crest stem cells in the adult mammalian hair follicle. We discovered that numerous neural crest cells reside in the outer root sheath from the bulge to the matrix at the base of the follicle. Specifically, found that bulge explants from adult mouse whisker follicles yield migratory neural crest cells, which in clonal culture form colonies consisting of over thousand cells. We confirmed that these clone forming cells are multipotent capable of differentiating into an entire array of cranial neural crest cells including neurons, smooth muscle cells, rare Schwann cells and melanocytes.

In this regard, as detailed below, we achieved targeted differentiation of these multipotent clone forming cells into Schwann cells and cartilage/bone cells with neuregulin-1 and bone morphogenetic protein-2 (BMP-2), respectively. We also demonstrated through in vitro serial cloning that the claimed multipotent cells were capable of self-renewal. Together, the data presented in this example show that the adult mouse whisker follicle contains multipotent epidermal neural crest stem cells (EPI-NCSCs), which are promising candidates for diverse cell therapy paradigms because of their high degree of inherent plasticity and easy accessibility in the skin.

Neural Crest-Derived Cells in the Embryonic and Postnatal Facial Skin

FIG. 1 shows sections through embryonic and postnatal Wnt1-cre/R26R facial skin of an embryonic day (E) 16.5 double transgenic embryo. Neural crest-derived cells are identified by their blue Xgal-reaction product. In the face many structures are of neural crest origin. This includes the facial dermis (FIG. 1A, d), the dermal papilla of hair follicles (FIG. 1A, dp), but not the epidermis (FIG. 1A; ed). The whisker follicle is surrounded by blood sinuses (FIG. 1A, bs), the connective tissue of which is also of neural crest origin. The hair follicle represents an invagination of the basal layer of the epidermis. The basal layer of the epidermis is single cell layer except in the bulge region where it is multi-layered. The inner layers of the bulge, which is a niche for epidermal stem cells, contain neural crest cells as well. Some neural crest cells within hair follicles form streams that extend from the bulge region to the base of the follicle, which contains the matrix that forms the new hair (FIG. 1B, arrow; higher magnification of area marked at the left in A), suggesting that neural crest cells migrate within the hair follicle. A large number of neural crest cells reside in the bulge region both of embryonic (FIG. 1C, arrow; E16.5) and postnatal anagen whiskers (FIG. 1D, arrow; postnatal day 24). Since melanocytes within hair follicles provide melanin to the growing hair, the matrix is expected to contain neural crest cells. Xgal-positive neural crest cells are indeed present in the matrix of whiskers both from newborn (FIG. 1E; arrows) and adult (FIG. 1F, arrows; cross section) mice. Many of them contain pigment granules (FIG. 1E, e.g. arrows). In summary, there are neural crest cells localized in the epidermis of the whisker follicle along the entire length of the follicle, both prenatally and postnatally.

Neural Crest Cells Emigrate from Bulge-Explants

Figure 2:
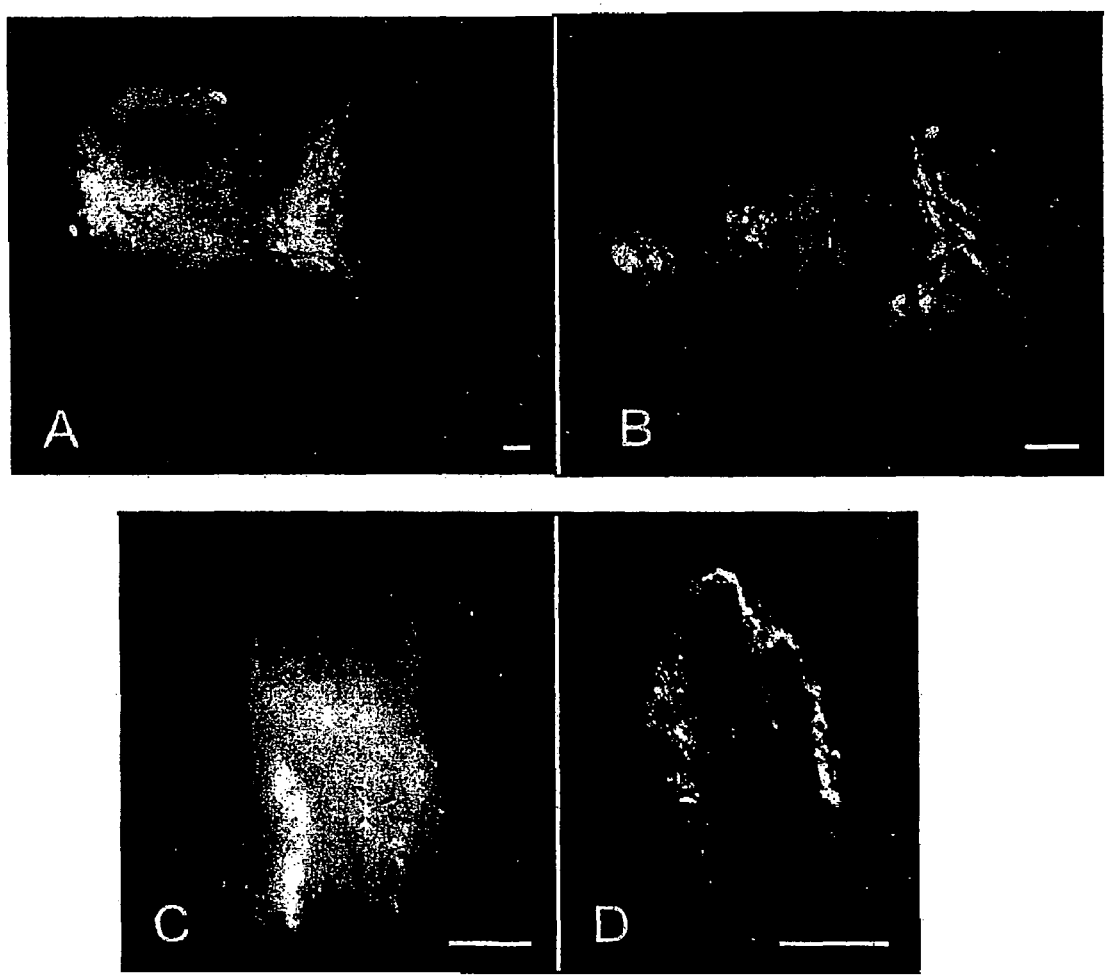
FIG. 2 shows dissection of the bulge from adult whisker follicles. (A) Dissected follicle surrounded by dermis and fat tissue. On the left the dark matrix and on the right the hair are visible. (B) Dissected whisker follicle devoid of dermis. On the right, below the skin, the ring sinus and on the left the cavernous sinus are visible. (C) Bulge within the connective tissue capsule. (D) Isolated bulge. Bars, 100 µm.

The objective of this study was to determine by in vitro clonal analysis the developmental potentials of the neural crest cells that reside in the bulge area, which is a known niche for keratinocyte stem cells (Oshima et al., 2001) and melanocyte stem cells (Nishimura et al., 2002). To this end we microdissected the bulge area. Whiskers were dissected from the skin (FIG. 2A), and the dermis and fat tissue were then removed mechanically and with buffer rinses (FIG. 2B), exposing the ring sinus below the skin and the cavernous sinus near the base of the follicle. The capsule of the whisker was cut longitudinally, and subsequently the follicle was transected both above the cavernous sinus and below the skin, which yielded the bulge area within the collagen capsule (FIG. 2C). Finally, the bulge region was rolled out of the capsule (FIG. 2C) and placed into a collagen-coated culture plate, where it adhered to the substratum within 1 hour.

Figure 3:
FIG. 3 shows a bulge explant. Xgal-reacted explant 4 days post-explantation. (A) Phase contrast image of a bulge explant. The explant with the hair still inside, and emigrated cells are visible. The explant got displaced away from the cells during mounting of the cover slip. (B) The same bulge explant with focus on the bulge. Numerous Xgal-positive neural crest cells are present within the bulge. (C) Area marked at the right in (A) shown with phase contrast optics. (D) Corresponding bright field image. All emigrated cells are Xgal-positive, proving their neural crest origin. (E) Area marked on the left in (A) shown with phase contrast optics. (F) Corresponding image with bright field optics. All cells are Xgal-positive. Bars; (A), 100 µm; (B) 100 µm, (C-F), 100 µm.
Figure 4:
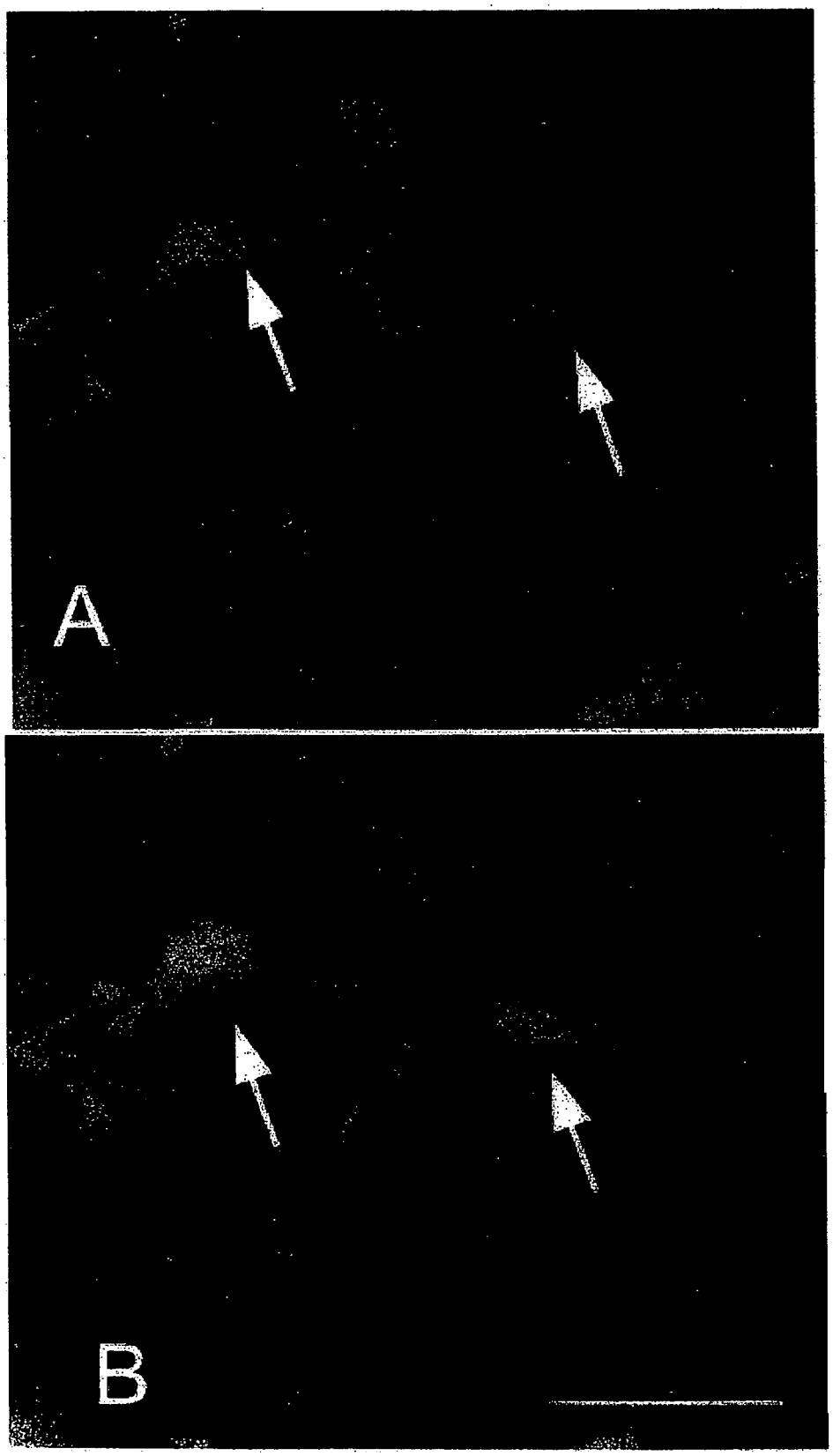
FIG. 4 shows Sox10 expression in bulge explants. Sox10 is a marker for early migrating neural crest cells. All cells that have emigrated from bulge explants express Sox10 at high levels, confirming that they are neural crest cells. Bar, (A, B), 50 µm.

FIG. 3 shows a bulge explant 4 days post-explantation. In FIG. 3A, the explant and the emigrated cells are shown with phase contrast optics. FIG. 3B shows a higher magnification with focus on the explant. Numerous Xgal-positive neural crest cells are present within the bulge. FIG. 3C shows at higher magnification the area to the right marked in A FIG. 3D is the corresponding bright field image, showing that all cells are Xgal-positive. FIG. 3E shows with phase contrast optics the area to the left marked in (A). FIG. 3F is the corresponding bright field image, which shows that all cells are Xgal-positive. At 48 hours post-explantation 0-15 cells, and at 72 hours 126.8±41.5 cells per explant are present on average. The increase in cell numbers over time is due to emigration of new cells and concomitant rapid proliferation (initial doubling time approximately 6 hours). Bulge explants from wild type and single-transgenic littermates are Xgal-negative. Emigrated cells also express Sox10, a marker for neural crest cells (FIG. 4; Kuhlbrodt et al., 1998; Rehberg et al., 2002), which confirms the neural crest origin of the cells that emerge from bulge explants.

Bulge Explant-Derived Neural Crest Cells are Multipotent

In vitro clonal analysis established that neural crest cells from bulge explants are multipotent. FIG. 5A-D shows the time course of a clone as it grows during the first 3 days: (A) 6 hours, (B) 18 hr, (C) 48 hr, and (D) 72 hr after cloning. Six hours after cloning, cells have a stellate morphology (FIG. 5A) and an initial doubling time of approximately 6 hours, which in subsequent days increases to 12-24 hours. At 24 hours of clonal culture, clones contain 4-16 cells. The continuously changing shape of the clone illustrates the high cell motility (FIG. 5). By two weeks of culture, this type of colony consists of thousands of cells and constitutes 83.0±2.7% of all colonies (Table 2). The remaining 17% of colonies are small, consisting of 4-8 cells and contain one of two types cells, either flattened cells that resemble smooth muscle cells, or unidentified small elongated cells.

TABLE 2

Percent of primary and secondary clones formed

| Clone Type | Clones formed by stem cells (% of total ± S.E.M) |
| --- | --- |
| Primary (from day 4 bulge explants) | 83.0 ± 2.7¶* |
| Secondary (from day 3 primary clones) | 73.5 ± 6.7¶§ |
| Secondary (from day 5 primary clones) | 66.2 ± 4.4*§ |

Average number of cells per primary clone at the time of subcloning

Figure 6:
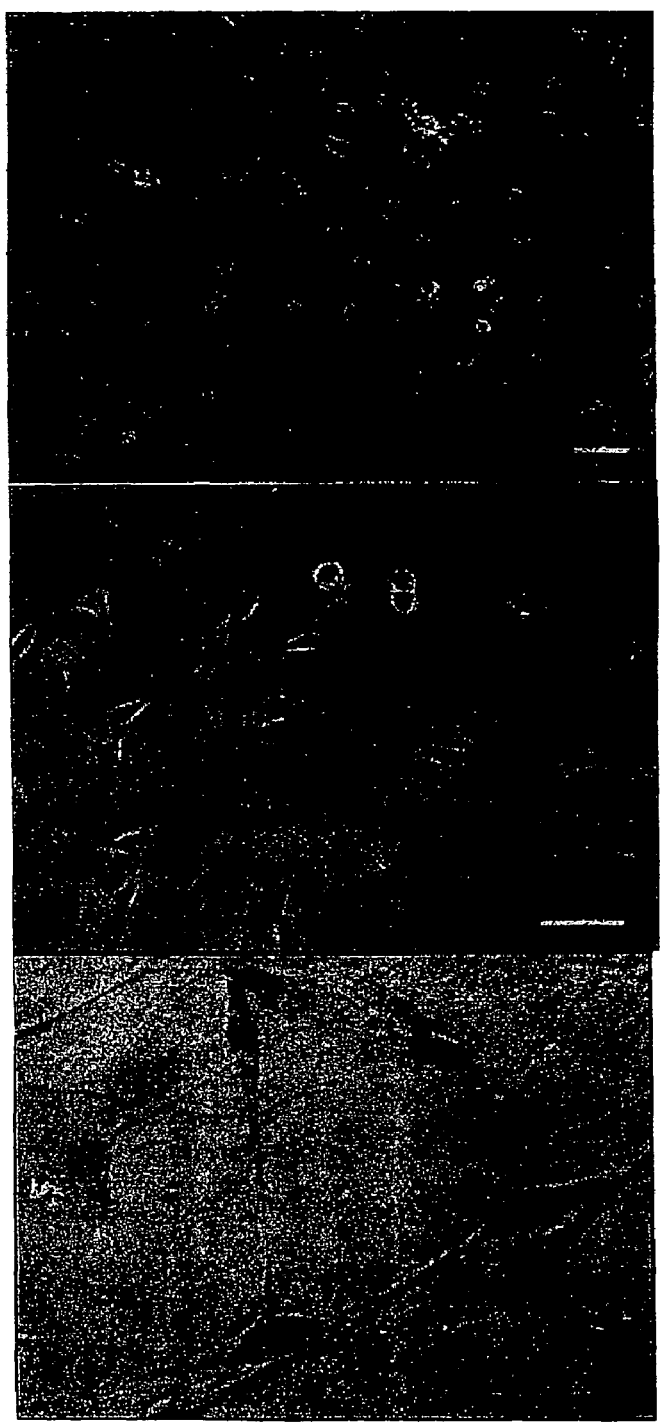
FIG. 6 shows clones at 2 weeks in clonal cultures. At 2 weeks in clonal culture, colonies consist of thousands of cells. (A) shows a small part of a 2-week-old clone. Most cells are elongated. (B) Higher magnification of a different area. Some cells are large and flattened (arrowhead). Proliferating cells are still present (see postmitotic doublet marked by arrow). (C) All cells in clones are Xgal-positive (Hoffmann contrast optics), confirming that they are neural crest-derived cells. Bars, (A-C) 50 µm.
Figure 7:
FIG. 7 shows differentiated cell types expressed in a clone. (A, B) Quadruple stain combining anti-neuron-specific beta-III tubulin antibodies (Texas red) with anti-smooth muscle actin monoclonal antibody (fluorescein), DAPI nuclear stain (blue) and Xgal-reactivity (shown in B). Several neurons and one smooth muscle cell are visible (focus is on neurons). (B) Xgal reaction of two areas marked in A. (C) Smooth muscle cell (anti smooth muscle actin antibody; Texas red). (D) Rare SCIP-immunoreactive Schwann cell. (E) Corresponding phase contrast image. (F) Rare S100-immunoreactive Schwann cell progenitor. (G) Corresponding phase contrast image. (H) Three MelEM-immunoreactive melanocyte progenitors. (I) Corresponding phase contrast image. Bars (A-I) 50 µm.

At two weeks of culture, many cells in clones exhibit long processes (FIG. 6A-C). Others resemble morphologically mature smooth muscle cells (FIG. 6B, arrowhead). Many proliferating cells are still present at two weeks in clonal culture (see doublet of late anaphase cells in FIG. 6B; arrow) and all cells are Xgal positive (FIG. 6C). To identify different cell types, clones were first processed for Xgal reaction and subsequently for immunocytochemistry with cell type specific antibodies. Cells with long processes are intensely immunoreactive for neuron-specific beta-III tubulin FIG. 7A). FIG. 7B shows Xgal reactivity in the areas marked in FIG. 7A. The Xgal reaction product is most intense in, and often limited to, inclusion bodies, as has been described previously by Rico et al., (2002) and Szeder et al. (2003). Large flattened cells are immunoreactive for smooth muscle actin (FIG. 7A, fluorescein; (C), Texas red). Rarely, clones also contain Schwann cell progenitors as shown by SCIP immunoreactivity (FIG. 7D, E; Zorick et al., 1996) and S100 immunoreactivity (FIG. 7F, G; Parkinson et al., 2001). The presence of pigment cell precursors in clones is documented by MelEM-immunoreactivity (FIG. 7H, I; Nataf et al., 1993; Alexanian and Sieber-Blum, 2003). The differentiation of multiple cell types within clones demonstrates that bulge-derived neural crest cells are multipotent.

Targeted Differentiation into Schwann Cell Progenitors

Figure 8:
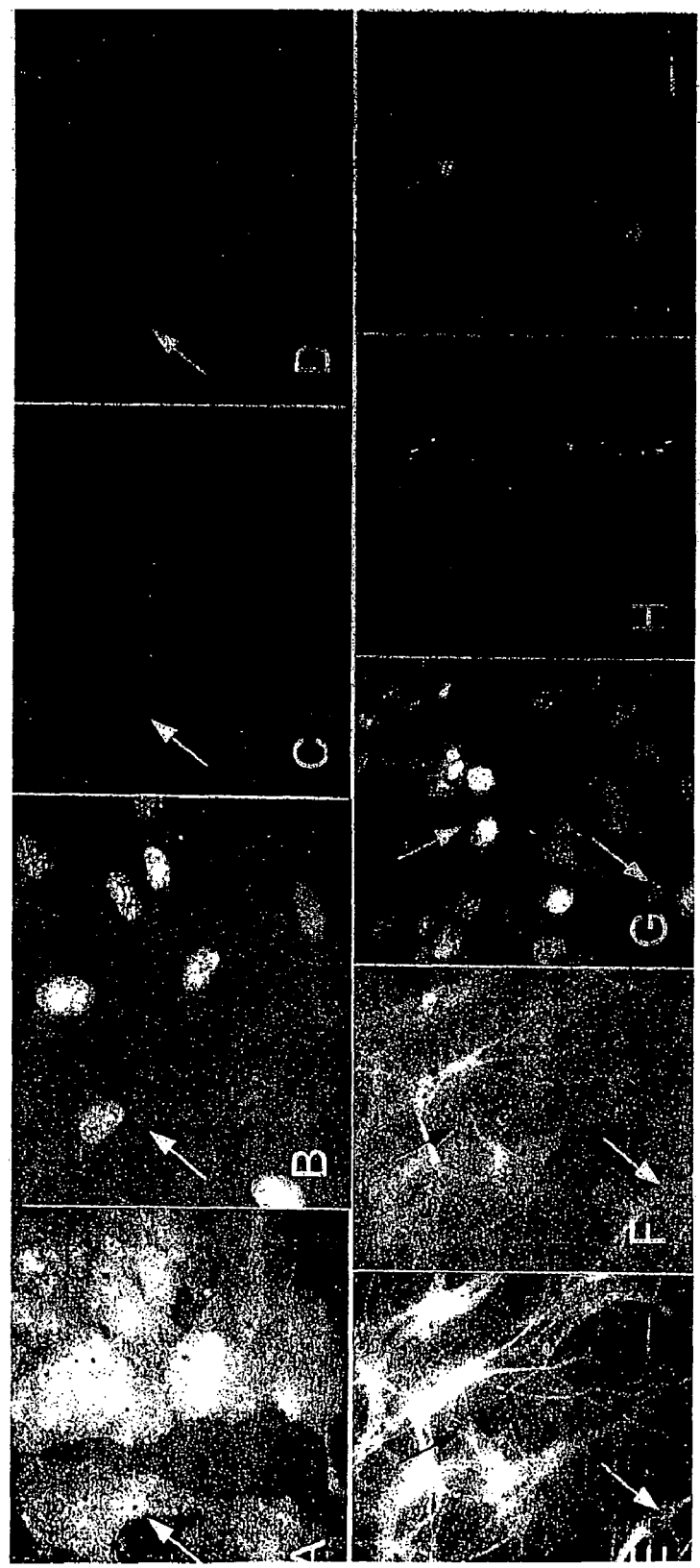
FIG. 8 shows targeted differentiation of EPI-NCSCs into Schwann cell progenitors. In order to obtain larger numbers of Schwann cell progenitors, clones were grown in the presence of neuregulin-1. Quadruple stain combining beta-III tubulin (fluorescein), GFAP (Texas red), DAPI nuclear stain (blue) and Xgal-reaction (black). (A) GFAP stain with Xgal reaction product (e.g. arrow). Several Schwann cell progenitors are visible. (B) DAPI nuclear stain of same area as in (A). (C) beta-III tubulin immunoreactivity (Texas red) in the same area is absent. Arrow depicts same cell and Xgal reaction product as in (A) and (B). (D) Merged images of GFAP (Texas red), beta-III tubulin (fluorescein, absent), DAPI nuclear stain and Xgal reaction. This series of images shows that Schwann cell progenitors are present in large numbers and that they do not express a neuronal marker. In a different area in the same clone neurons are present: (E) beta-III tubulin stain; several multipolar neurons are present. (F) Merged bright field and beta-III tubulin images of the same area as in (E) to show that neurons contain Xgal-reaction product (arrow in E, F, C and I). (G) Corresponding DAPI nuclear stain. (H) GFAP immunoreactivity in the same area is absent (Texas red). (I) Merged images in pseudocolor of beta-III tubulin (fluorescein), GFAP (Texas red, absent), DAPI nuclear stain (blue). The data show that neurons do not express a Schwann cell marker. Bar, 10 µm.

It has been reported that neuregulin promotes differentiation of neural crest cells into Schwann cells (Shah et al. (1994)). In the presence of neuregulin-1 (10 nM), clones contain large numbers of Schwann cell progenitors, and neurons are present as well. FIG. 8 shows a quadruple stain that combines glia fibrillary acidic protein (GFAP; Schwann cell marker) immunoreactivity (Texas red) with beta-III immunoreactivity (fluorescein), DAPI nuclear stain and Xgal reaction. FIG. 8A-D focuses on a group of GFAP-positive Schwann cell progenitors: (A), GFAP Texas red) immunoreactivity; (B) DAPI: (C) beta-III tubulin (fluorescein; absent). (D) shows merged images in pseudocolor. FIG. 8E-I shows a group of neurons in a different area of the same clone: (E), beta-III tubulin immunoreactivity; (F) merged bright field and fluorescein images to better visualize the Xgal reaction product within neurons (e.g., arrows), (G) corresponding DAPI stain; and (H) GFAP immunofluorescence (absent). FIG. 8I shows merged images in pseudocolor.

Taken together, the data show that while Schwann cell progenitors rarely develop in our regular culture medium, their number increases greatly in the presence of neuregulin-1, which suggests that neuregulin-1 directs epidermal neural crest stem cells to differentiate along the Schwann cell lineage. Furthermore, the data in FIG. 8 show that neurons do not express a glia marker and Schwann cell progenitors do not express a neuronal marker. In summary, when EPI-NCSCs are grown in the presence of neuregulin, numerous Schwann cell progenitors develop, as well as neurons and possibly other types of cell.

Targeted Differentiation into Chondrocytes

Figure 9:
FIG. 9 shows targeted differentiation of EPI-NCSCs into chondrocytes. To determine if EPI-NCSCs are able to generate chondrocytes, we grew clones in the presence of bone morphogenetic protein-2 (BMP-2). After 2 weeks in culture many cells in clones were immunoreactive for collagen type-II, a marker for cartilage/bone cells. Triple stain combining collagen type II immunoreactivity (Texas red), Xgal-reaction (black) and DAPI nuclear stain (blue). (A) Collagen type II immunoreactivity. Six cells are visible and they contain Xgal reaction product (e.g. arrows). (B) Merged images in pseudo-color of collagen type II immunoreactivity (Texas red), DAPI (blue) and Xgal (black). (C) Bright field image of the same area as in (A) and (B) to better visualize the Xgal reaction product (e.g. arrows). Bar, 50 µm.

To determine whether bulge-derived neural crest cells can generate the full spectrum of cranial neural crest derivatives, we sought to differentiate them into chondrocytes. Sox9 is required for the commitment of neural crest cells to the chondrogenic lineage (Mori-Akiyama et al., 2003) as it is a potent activator of type II collagen expression in chondrocytes (Kypriotou et al., 2003). BMP-2 causes robust up-regulation of Sox9 (Zehentner et al., 2002). We therefore cultured bulge-derived neural crest cells in the presence of BMP-2 (10 ng/ml) for 2 weeks in clonal culture. Under these conditions, most cells in clones become collagen type II-immunoreactive, indicating that they have differentiated into chondrocytes. FIG. 9A shows a group of collagen type II-immunoreactive cells with Xgal reaction product (arrows). FIG. 9B shows merged images of collagen type II immunoreactivity (Texas red), DAPI (blue) and Xgal (black; arrows). FIG. 9C shows the same area with bright field optics to better visualize the Xgal reaction product. The data show that BMP-2 directs bulge-derived neural crest cells in clonal culture to differentiate along the chondrogenic cell lineage.

Verification of Neuronal and Schwann Cell Differentiation by RT-PCR

Figure 10:
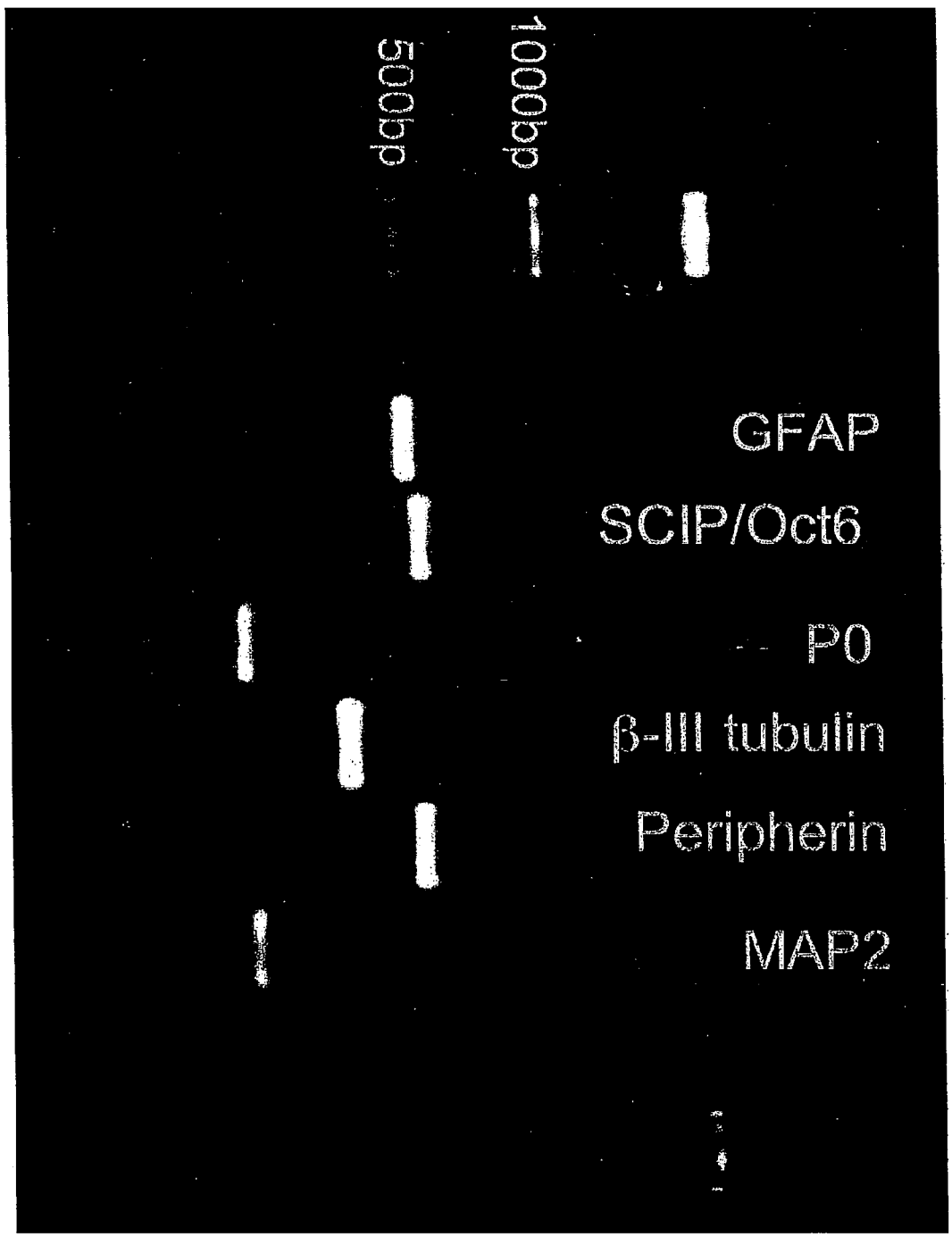
FIG. 10 shows RT-PCR to detect Schwann cell and neuron specific gene expression. In cells grown in the presence of neuregulin (10 nM), GFAP, SCIP/Oct6 and P0 were abundantly expressed. Likewise, in cultures that were grown in non-supplemented culture medium, the neuronal genes beta-III tubulin, peripherin and MAP2 were expressed.

To establish the specificity of the antibody stains and to test additional neuronal markers by different means, we performed RT-PCR for 3 neuronal and 3 Schwann cell markers. Bulge-derived cells grown for two weeks in culture medium supplemented with neuregulin-1 express the Schwann cell markers GFAP, SCIP/Oct6 and P0 abundantly (FIG. 10). Cells that were grown in regular culture medium in the absence of neuregulin-1 express beta-III tubulin, peripherin and MAP2 (FIG. 10). The authenticity of the RT-PCR products were verified by sequencing.

Bulge-Derived Neural Crest Cells can Undergo Self-Renewal

Figure 11:
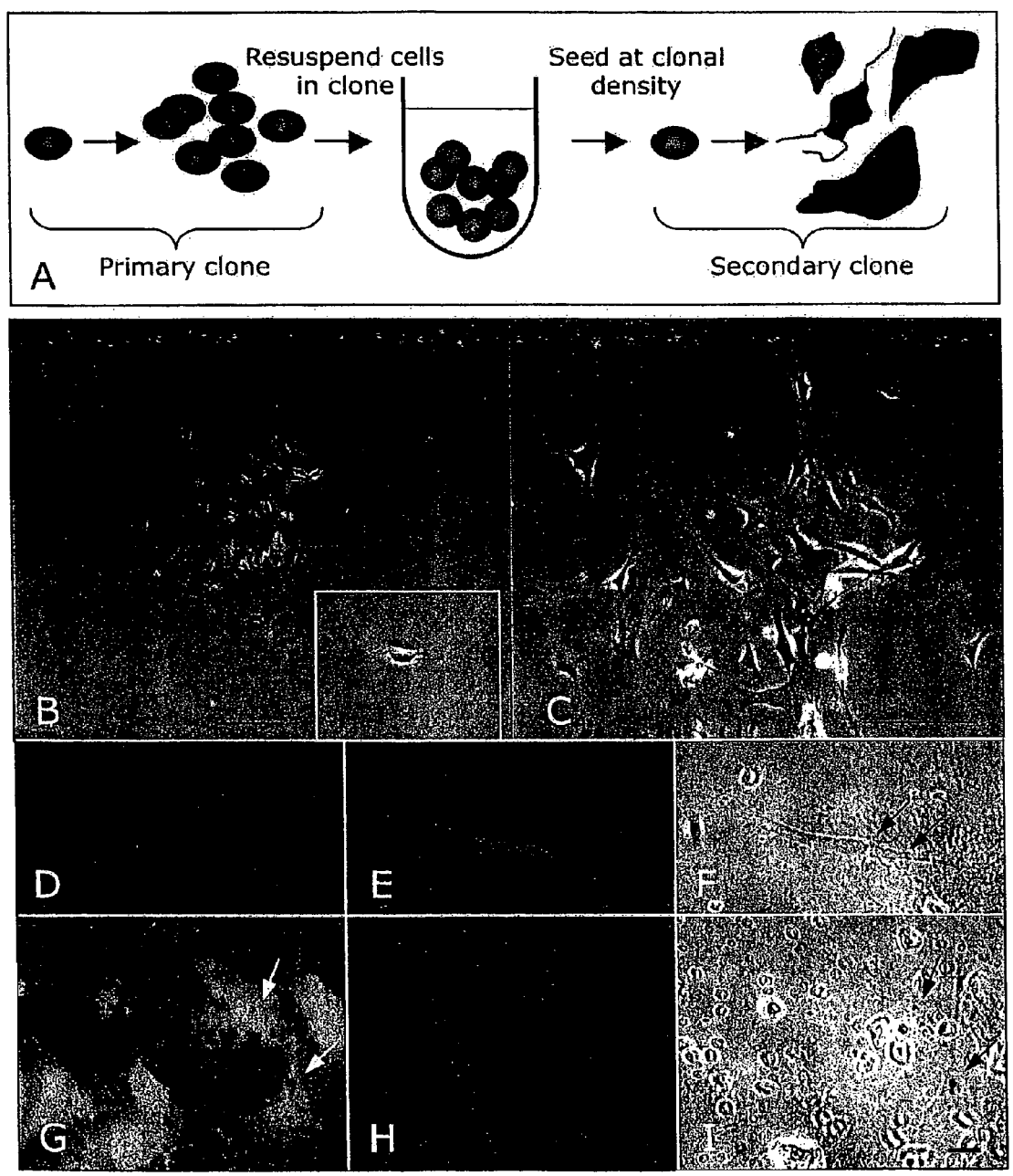
FIG. 11 shows serial cloning to determine that bulge-derived neural crest cells can undergo self-renewal. (A) Cells from primary bulge explants were put into clonal culture and let grow into a colony (primary clone). Clones were subsequently isolated by putting a glass cloning ring around them and they were then resuspended by adding 2 drops of 0.025% trypsin and 0.02% EDTA in phosphate buffered saline. When the cells detached, trypsinization was stopped by 1 mg/ml of trypsin inhibitor in culture medium. The cells were aspirated, diluted with 1.5 ml of culture medium and placed into a new collagen-coated 35 mm plate (secondary clones). Plates with secondary clones were grown for 2 weeks and then analyzed with cell type-specific antibodies. (B) Five day-old secondary clone. Insert; the secondary-clone-forming cell. (C) Higher magnification of area marked in (B). Cell morphology in secondary clones resembles that in primary clones. After two weeks, secondary clones were fixed and processed for immunocytochemistry. (D-I) Triple stain combining beta-III tubulin (Texas red) with smooth muscle actin (fluorescein) and Xgal reaction (black). (D) Smooth muscle actin (fluorescein) immunoreactivity; beta-III tubulin stain is absent. (E) beta-III tubulin stain in same area as in D shows one neuronal cell. (F) The corresponding phase contrast image shows Xgal reaction product (arrows). (G) Smooth muscle actin immunoreactivity (fluorescein) shows several smooth muscle cells in a different area of the same secondary clone. (H) Same area as in G, but with Texas red illumination. Smooth muscle actin-immunoreactive cells do not express the neuronal marker. (I) corresponding phase contrast image with Xgal reaction product (arrows). Bars, (B), 100 µm; (C), 100 µm; (D-I), 10 µm.

We determined whether bulge-derived neural crest cells can undergo self-renewal by serial cloning in vitro. For this primary clones were prepared. Three or 5 days later, primary clones were resuspended by trypsinization with the aid of a glass cloning ring. The resuspended clone was seeded again at clonal density (20-50 cells per 35 mm culture plate) and incubated for 2 weeks (FIG. 11A). FIG. 11B shows a 5 day-old secondary clone. The insert shows the secondary clone-forming cell shortly after plating at higher magnification. FIG. 11C shows a higher magnification of the area marked in (B). The morphology of cells in secondary clones is similar to that in primary clones and in primary explants. At the end of the culture period, secondary clones were analyzed with cell type specific antibodies. FIG. 11D-I shows a triple stain that combines Xgal (F, I; black dots; arrows) with beta-III tubulin (E; Texas red) and smooth muscle actin (G; fluorescein) antibodies. A beta-III tubulin-immunoreactive neuronal cell is shown in (E); it does not express smooth muscle actin (D). In a different area of the same secondary clone, a group of smooth muscle cells (G) is present, which do not express beta-III tubulin (H). The data indicate that the primary clone contained stem cells, which were able to generate at least 2 distinct differentiated cell types, which fulfills the criterion for self-renewal.

Primary clones from day 4 bulge explants, comprise 83.0±2.7% of all colonies. The percentage of secondary clones formed by multipotent cells is 73.5±6.7% when taken from day 3 primary clones and 66.2±4.4% when prepared from day 5 primary clones (Table 2). Thus the portion of stem cells is maintained at relatively high levels over an estimated total of 18 doublings in primary and clonal culture, despite the fact that our culture medium was developed to support the differentiation of neural crest cells (Ito and Takeuchi, 1984; Ito et al., 1993). Taken together, we have shown that bulge-derived neural crest cells are multipotent and that they can undergo self-renewal. Thus, bulge-derived neural crest cells fulfill the criteria for multipotent stem cells (EPI-NCSCs).

Figure 12:
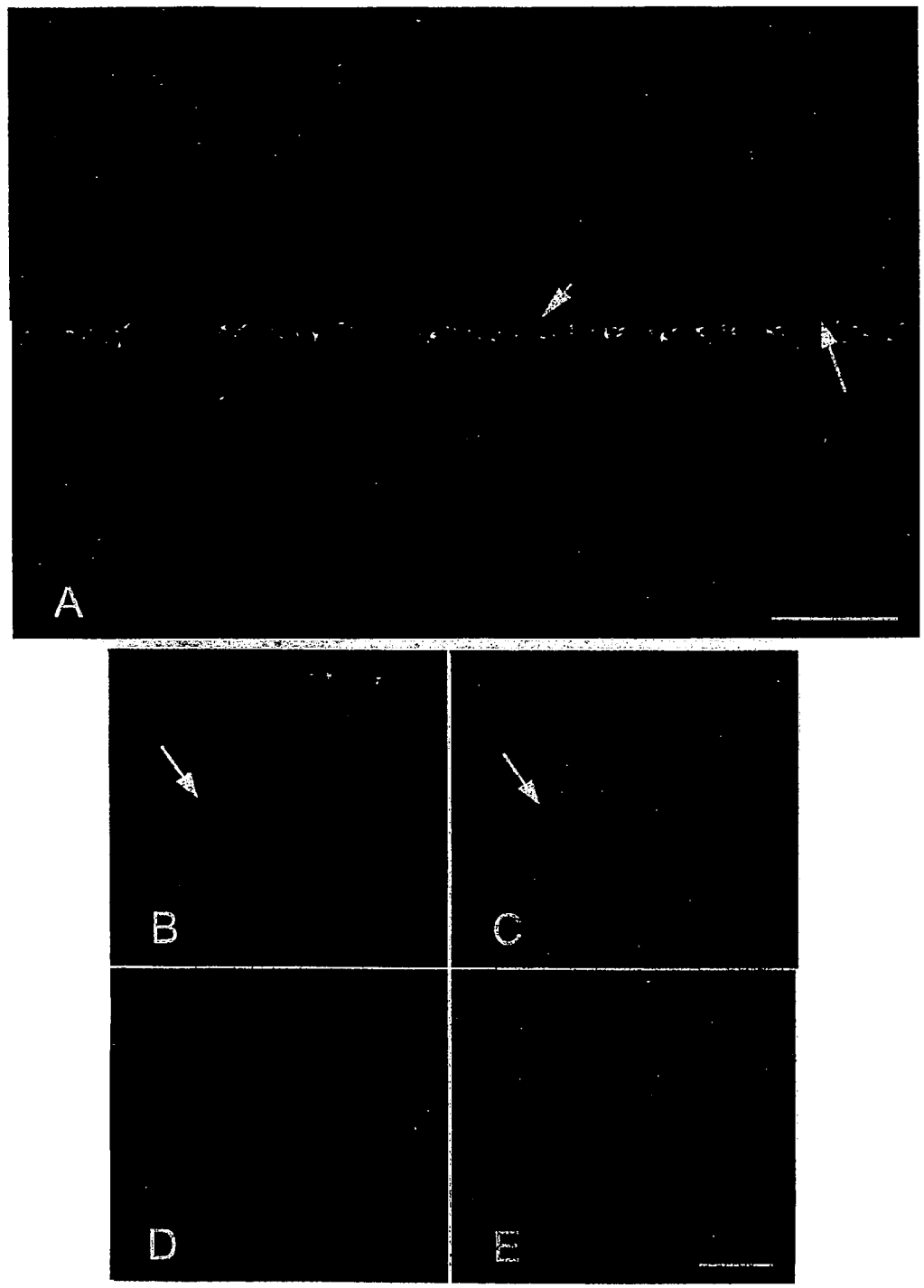
FIG. 12 shows that EPI-NCSCs and adult Schwann cell progenitors are distinctly different types of cells. Whisker follicles are innervated by myelinated nerves. Thus our preparation could be contaminated by myelinated nerve endings. To determine if EPI-NCSCs are adult Schwann cell progenitors we compared EPI-NCSCs with Schwann cell precursors from adult sciatic nerve explants. (A) Nestin/DAPI double labeling in day 5 bulge explant. Virtually all cells, in particular stellate cells (e.g. long arrow), are intensely nestin immunoreactive (Texas red). Cells with the morphology of differentiating smooth muscle cells (short arrow) express lower levels of nestin. (B) By contrast, cells at culture day 5 that had emigrated from adult sciatic nerve explants express nestin at low levels only, or not at all (e.g. arrow; Texas red). (C) The same cells were, however, intensely immunoreactive for SCIP (fluorescein fluorescence), a marker for Schwann cell progenitors (Zorick et al, 1996), whereas EPI-NCSCs rarely express SCIP-immunoreactivity under these culture conditions (FIG. 7D). (D) Nestin/DAPI merged images of area shown in (B) and (C). (E) SCIP/DAPI merged images of area shown in (B), (C) and (D). (A) Bar, 50 µm. Bar (B-E) 50 µm. The data indicate that EPI-NCSC are distinctly different from nerve-derived Schwann cell progenitors.

EPI-NCSC are Distinctly Different from Schwann Cell Progenitors of the Adult Sciatic Nerve Since whiskers follicles are innervated by myelinated nerves, we sought to determine whether EPI-NCSCs are in fact Schwann cell progenitors derived from contaminating nerve endings. We therefore determined similarities and differences between cells that emigrate from whisker bulge explants and from sciatic nerve explants from adult mice. Both types of tissue were cultured under the same conditions in regular culture medium. Nestin is a marker for both neural stem cells (Lendahl et al., 1990) and neural crest stem cells (Lothian and Lendahl, 1997; Mujtaba et al., 1998; Josephson et al., 1998). As expected, bulge-derived cells express nestin at high levels (FIG. 12A; e.g. arrow). Differentiating cells with smooth muscle cell morphology expressed nestin at lower levels (A, arrowhead). By contrast, cells that have emigrated from adult sciatic nerve explants express nestin at low levels only, or not at all (FIG. 12B, e.g. arrow). Whereas SCIP-positive cells are observed only very rarely in bulge-derived cultures (FIG. 7D, E) under these culture conditions, all sciatic nerve derived cells express SCIP at high levels. FIGS. 12C and E show SCIP expression in the same cells shown in FIGS. 12B and D.

At 24 hours of clonal culture, 73.7±4.9% of sciatic-nerve derived colonies consist of 1-2 cells with Schwann cell-like morphology. These cells die within the second 24 hours in clonal culture, suggesting that they were dependent on axonal contact. The remaining 26.3% of colonies contain 9.3±0.9 cells per clone at 48 hours and 12.8±1.6 cells at 72 hours in clonal culture, suggesting a low rate of proliferation that is possibly combined with cell death.

Thus, while EPI-NCSCs have a high rate of proliferation and express nestin at high levels but not SCIP, sciatic nerve-derived cells have a lower rate of proliferation under the same culture conditions, most of them die within the first 48 hours, and they are intensely immunoreactive for SCIP, but not for nestin. These observations demonstrate that adult bulge-derived neural crest cells and adult sciatic nerve-derived Schwann cell progenitors are distinctly different types of cell.

EPI-NCSCs are Different from Merkel Cells

Located in the bulge region of the mammalian hair follicle are a variety of cells, including EPI-NCSCs and Merkel cells. In particular, Merkel cells are located exclusively in the outermost (basal) layer of the outer root sheath of the follicles of large hair (whiskers or sinus hair). Each follicle contains several hundred Merkel cells in the bulge region. Merkel cells are also located in the rete ridge (the opening of the hair follicle at the surface skin) and in interfollicular areas. To determine if mammalian Merkel cells are neural crest derivatives, Wnt1-cre/R26R double transgenic mice were employed, in which neural crest cells are specifically marked by the expression of beta-galactosidase. Beta-galactosidase co-localized with Merkel cells that were identified by cytokeratin 8 and 18, proving the neural crest origin of Merkel cells in mammals.

Further, we double stained whisker follicles with antibodies against Math 1 and CK8 to search for a Merkel precursor marker. Math 1 (recently renamed as Atoh1) is a transcription factor that is expressed in the nuclei of Merkel cell precursors during development. In the lower part of the whisker follicle, we found Merkel cells that co-expressed Math 1 (Atoh1) and CK8. The more superficial part of the follicle contained Math 1 positive cells that were CK8 negative, which are likely to represent Merkel cell precursors. Some of these cells express the cell proliferation marker, Ki-67 protein, which is not detected in mature Merkel cells. Specifically, Math1 (Atoh1)-positive cells that lack the expression of mature Merkel cell markers are proliferative Merkel cell precursors; however, Math1 (Atoh1)-positive cells that express Merkel cell markers are postmitotic Merkel cells. Accordingly, Math1 (Atoh1)-positive neural crest cells are cells of Merkel cell lineage.

Figure 13:
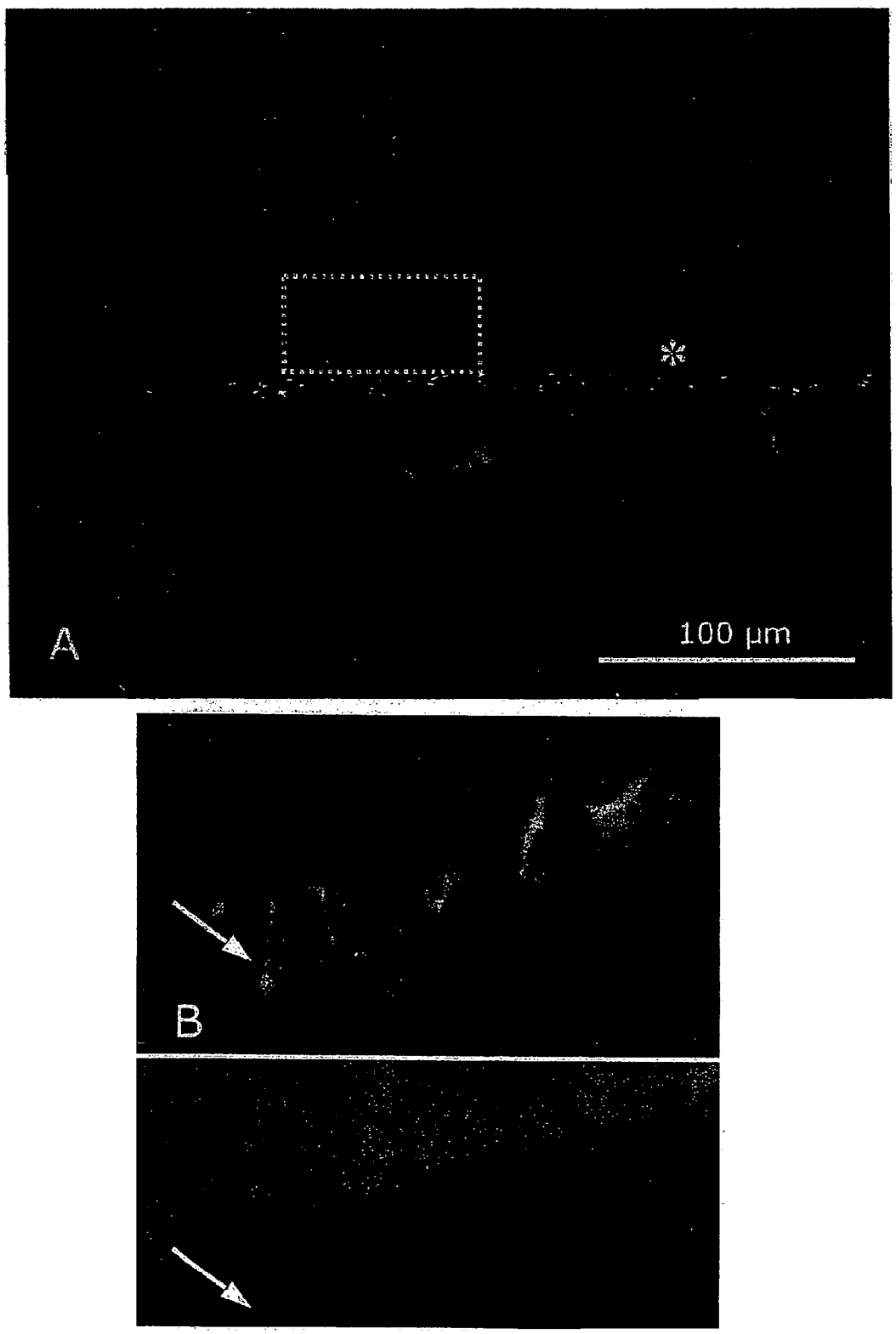
FIG. 13 shows Merkel cells are neural crest derivatives. E 16.5 Wnt1-cre/R26R double transgenic whisker follicle triple stained with antibodies against beta-galactosidase (Texas red), Troma-1 (fluorescein) and DAPI nuclear stain (blue). (A), merged image. (B), Troma-1 stain of area marked in (A) showing several Merkel cells. (C), beta-galactosidase stain of same area shown in (B). Merkel cells (e.g. arrow) also express beta-galactosidase (e.g. arrow), identifying them as neural crest derivatives (Szeder et al., 2003).

In FIG. 13, we illustrate in more detail the neural crest origin of Merkel cells (Szeder et al., 2003) in a tangential section through an E 16.5 whisker follicle. FIG. 13(A) shows merged images of a triple stain that consists of beta-galactosidase immunoreactivity (Texas red), Troma-1, a monoclonal antibody that recognizes cytokeratin 8, (a marker for Merkel cells) and DAPI nuclear stain (blue). FIG. 13(B) shows a higher magnification of the Troma-1 stain in the area marked in (A), whereas (C) shows the corresponding beta-galactosidase stain (Texas red) in the same area and focal plane. Troma-1 positive Merkel cells also express beta-galactosidase, identifying them as neural crest derivatives (Szeder et al., 2003). Thus, it is believed that Merkel cells are different from EPI-NCSCs, which are multipotent, highly proliferative cells themselves, capable of undergoing directed differentiation.

EPI-NCSCs Different from Skin Derived Precursors

We also wish to clarify that EPI-NCSCs are different from other skin-derived precursor cells isolated from human skin recently reported in the literature (see Toma et al., 2001 and 2005). Specifically, it has been reported that mouse back skin-derived precursor cells (SKP) (Toma et al., 2001) and human SKP-like cells (Toma et al., 2005) are observed in the dermis of hairy skin and non-hairy skin. As reported, this observation was made first during embryogenesis and at low levels and in low numbers in adulthood. In contrast, we note that the novel EPI-NCSCs of the invention are abundant in adulthood, as compared to the numbers reported by Toma et al. Furthermore, we have isolated EPI-NCSCs from various stages of early and advanced postnatal mouse development (i.e., 8 week-old to 6 month-old). In this regard, it is noted that the average life span of a mouse is only 3 years. We found no detectable difference in the yield of EPI-NCSCs isolated. An abundant number of EPI-NCSCs were isolated at all stages of post-embryonic mouse development, from childhood to adulthood. Thus, it is believed that SKP-cells are different from EPI-NCSCs.

Example 2

Neural Crest-Derived Cells in Hair of Adult Mouse Back Skin

In this example, we demonstrate that the claimed method can be used to isolate multipotent neural crest stem cells from different types of hair. This was accomplished as described in M. Sieber-Blum and M. Grim (2004) The Adult Hair Follicle: Cradle for Pluripotent Neural Crest Stem Cells, *Birth Defects Research* 72:162-172), which is incorporated by reference here in its entirety.

Figure 14:
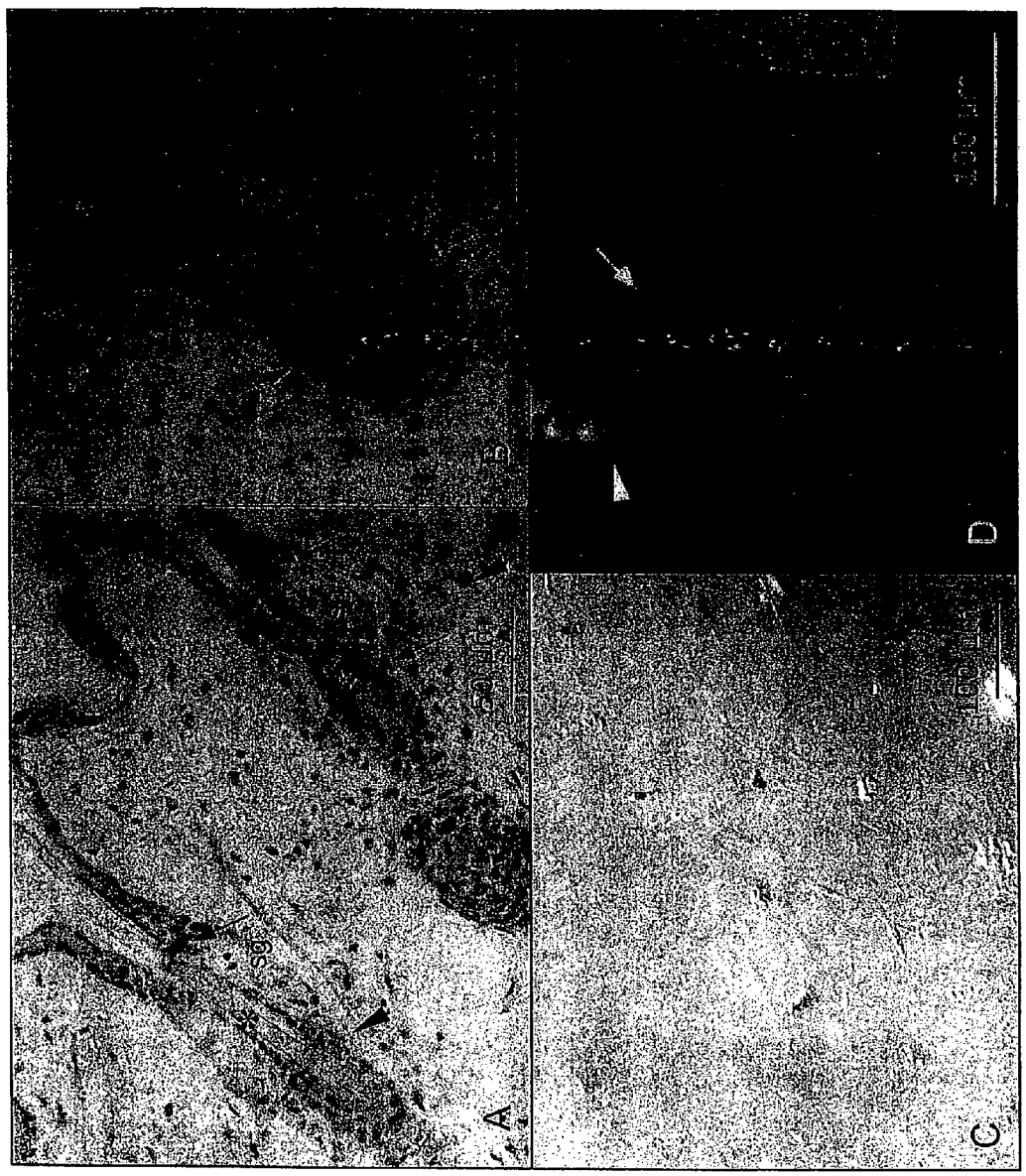
FIG. 14 shows the presence of neural crest-derived cells in hair follicles of back skin hair from adult mice. (A) Xgal stain through a section of adult double transgenic back skin, counterstained with nuclear red. Two hair follicles are visible. Xgal-positive neural crest-derived cells are visible above and below the bulge region (arrows). Xgal-positive cells marked with an arrowhead are Schwann cells ensheathing nerve fibers; sg, sebaceous gland. Hairs are marked with an asterisk. (B) Xgal-positive neural crest-derived cells are also present below the bulge region, near the base of the follicle (arrows). Hair is marked with an asterisk. As this were white double transgenic mouse (see white hair color), no melanocytes were present. (C) Colony of Xgal-positive neural crest-derived cells that was obtained from epidermis with adhering hair follicles cultured as floating pieces of epidermis (approximately 2×2 mm), which released cells that attached to the collagen substratum. (D) When such colonies were grown for 2-3 weeks, and subsequently probed with cell type specific antibodies, we identified neurons (beta-III tubulin Texas red immunofluorescence; e.g. arrow) and smooth muscle cells (smooth muscle actin fluorescein immunoreactivity; arrowhead). Both cell types contained also Xgal reaction product (see e.g., arrow and arrowhead). Fast-growing colonies of cells that were Xgal-negative were present as well. It was concluded that this method yields a mixture of neural crest-derived and non-crest cells.

Specifically, back skin of adult double transgenic mice (Wnt1-cre/R26R) is cut into small pieces (approx. 2×2 mm) and the epidermis is isolated by removing the dermis by collagenase treatment (2 mg/ml Hanks' balanced salt solution, 1 hr at 37° C.), and subsequent three rounds of low speed centrifugation (adapted from Toma et al., 2001 with modifications). Dermal cells remained in the supernatant and were discarded. The pieces of epidermis with attached hair follicles, which pierced the epidermis, were floated outside-up on top of the culture medium. At culture day 3, the floating epidermal pieces with attached skin follicles were removed. Starting at day 2 in culture, individual cells attached to the collagen substratum. They proliferated rapidly and gave rise to colonies containing hundreds of cells within neural crest derived-colonies form on the collagen substratum (FIG. 14C). Xgal reaction showed that there were blue colonies formed by neural crest derived cells, and also white colonies formed by non-crest cells, indicating that more than one type of progenitor cell is obtained with this method, which is not desirable.

When the neural crest derived-colonies are analyzed with cell type specific antibodies, the colonies contain neurons, smooth muscle cells and possibly other cell types. FIG. 14D shows merged images of a quadruple stain of a back skin-derived colony that combines neuron-specific beta-III tubulin immunofluorescence (Texas red; e.g. arrow), smooth muscle actin-immunoreactivity (fluorescein; arrowhead), and DAPI nuclear stain.

Also, the Xgal reaction products within the cells (e.g. arrow and arrowhead) show that neural crest-derived cells are present in the outer root sheath above the sebaceous gland and in the bulge region (FIG. 14A, arrows). Xgal staining is also seen at the base of the follicle (FIG. 14B). Xgal-positive Schwann cells, which are nerve-ensheathing cells, are visible as well (FIG. 14A, arrowheads). These observations show that EPI-NCSCs are not limited to whiskers, but that they occur in other types of hair as well, such as hair of the back skin of adult mice.

Example 3

Neural Crest-Derived Cells in Hair of Adult Human Skin

In this example, we demonstrate that in addition to using the claimed method to isolate neural crest stem cells from mouse (whiskers and back skin hair), the method is easily adapted to and equally applicable to primates, including human hair follicles.

Figure 15:
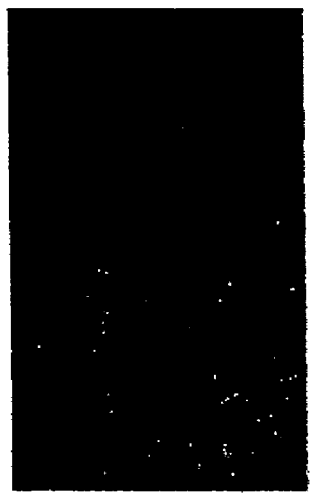
FIG. 15 shows dissected human hair (04103; 29 year-old male). (A) dissected scalp hair and (B) dissected pubic hair. The skin was cut into strips. The dermis was removed mechanically with sharpened tungsten needles and a small scalpel. Collagen fibers were cut with a scalpel and scissors, and finally the hair cut from the epidermis.
Figure 15:

Specifically, full-thickness skin (scalp and pubic) of a 29 year-old human male was cut into strips (FIG. 15). Collagen fibers were cut and removed with a scalpel, scissors and forceps. Dermal tissue was removed mechanically with bent sharpened tungsten needles, a small scalpel and flushes of Hanks' balanced salt solution. The dissected hair was cut from the epidermis. The dermal papilla was cut and removed and the dissected hair follicles placed into collagen-coated culture plates.

The culture medium was the same as for mouse neural crest stem cells, consisting of 85% Alpha-modified MEM medium, 5% chick embryo extract and 10% fetal bovine serum. The culture medium was exchanged with fresh medium every other day. Migratory cells with neural crest-like stellate morphology started to emerge from the explant 3-4 days post-explantation. Cells emigrated from many explants. Most cells had the morphology of neural crest cells (FIG. 16A).

Figure 17:
FIG. 17 shows Sox10 immunofluorescence in cells with neural crest morphology. (A) a phase contrast image shows the tip of a follicle explant and emigrating cells with neural crest-like morphology. The area marked with a rectangle in (A) is shown on the right (B) after staining with anti-Sox10 antibodies. Sox10 is a marker for neural crest cells. This indicates that emigrating cells with neural crest morphology are indeed neural crest cells. Emigrating keratinocytes do not express Sox10 (not shown).
Figure 17:
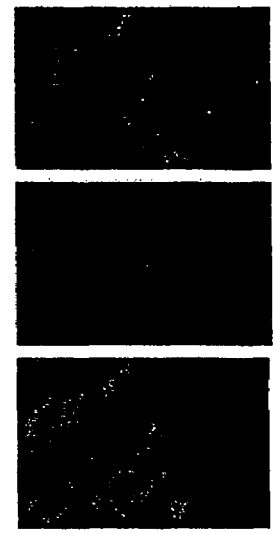
Figure 18:
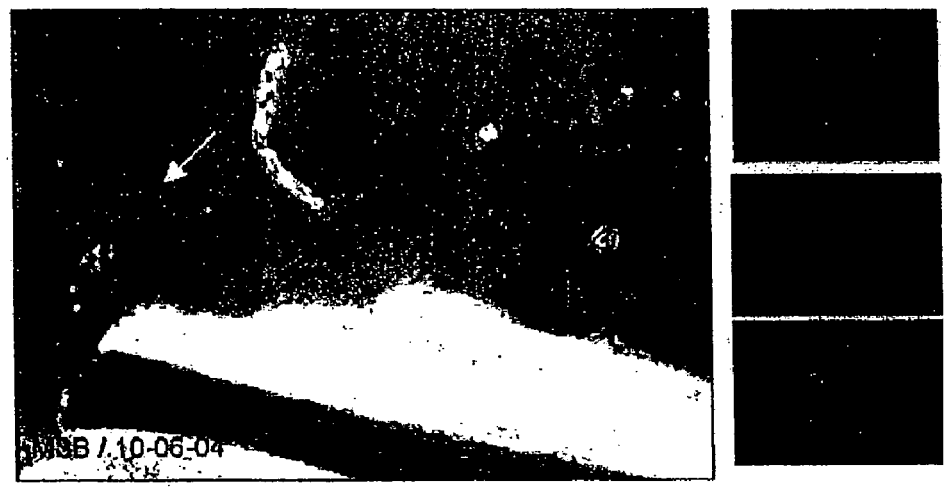
FIG. 18 shows human neural crest cell-like cells emigrating from follicle explants express nestin. Nestin is a marker for neural crest stem cells, among others. On the left (A) is a phase contrast image that shows a follicle explant and emigrating cells. The coarse background is due to collagen fibers of the substratum. The cell marked with an arrow in the left image (A) is shown in the right panels (B) to express nestin. The data thus suggest that neural crest cells that emigrate from human hair explants have stem cell characteristics. As expected, some keratinocytes express nestin also (not shown; see Li et al., PNAS 100, 9958, 2003).
Figure 19:
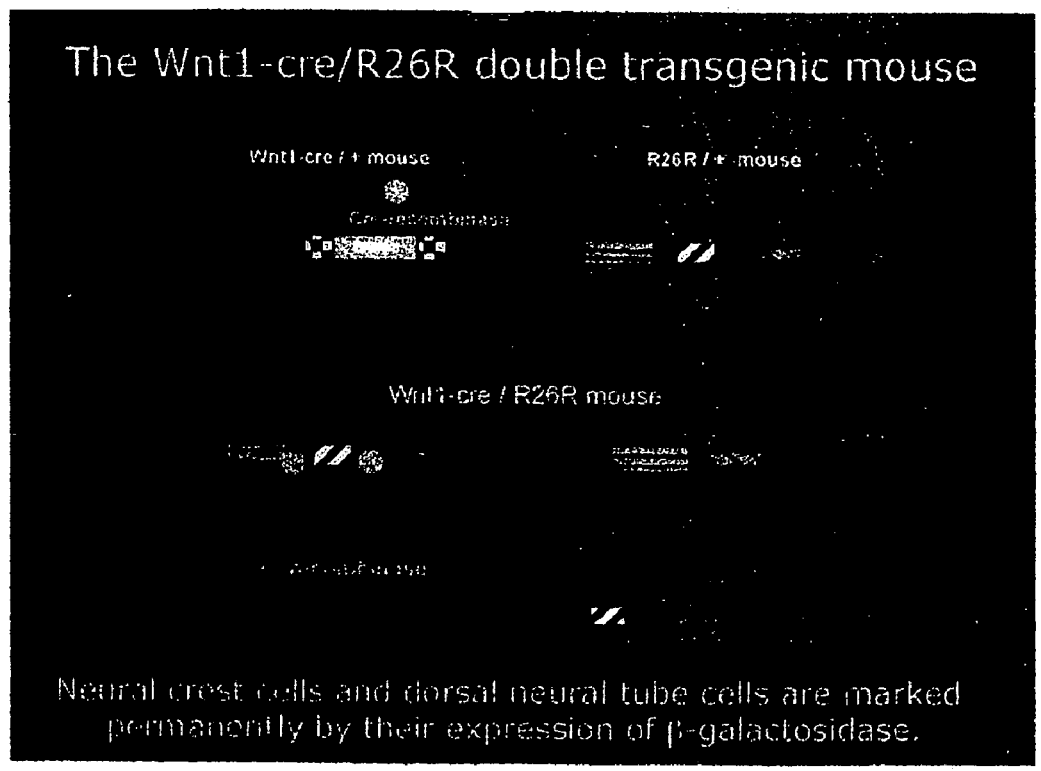
FIG. 19 shows Wnt1-cre/R26R double transgenic mouse genetics in which neural crest cells are specifically marked by their expression of beta-galactosidase.

It was also shown that human cells with neural crest morphology emigrating from follicle explants are indeed neural crest cells because they bind Sox-10 antibodies (FIG. 17). Sox10 is a marker for neural crest cells. Further, these emigrating cells express Nestin (FIG. 18). Nestin is a marker for neural crest stem cells, among others. These results indicate that using the claimed invention, neural crest cells can be isolated from human hair follicle explants (both scalp and pubic) having (1) neural crest morphology, (2) expressing neural crest marker, Sox10, and (3) stem cell marker, nestin, among others to be determined.

In summary, we have described efficient methods of isolating substantially pure EPI-NCSCs from the bulge region of non-embryonic (adult, juvenile and newborn) mammalian hair follicle. Since the neural crest is a transient tissue of the early embryo, the persistence of neural crest stem cells in post-embryonic bulge region of mammalian in hair follicles is surprising.

Example 4

Further Characterization of Neural Crest-Derived Cells in Mammalian Hair

Long Serial Analysis of Gene Expression (LongSAGE)

To gain a clear understanding of EPI-NCSC population, the cells were characterized by long serial analysis of gene expression (LongSAGE). Total RNA was isolated with Trizol reagent (Invitrogen, Carlsbad, Calif.) from approximately 60 neural crest cell explants and 100 bulge explants from adult mouse whiskers according to manufacturer's instructions. To avoid potential contamination with genomic DNA, the total RNA preparation was treated with DNase I (Invitrogen, Carlsbad, Calif.) as recommended in the manufacturer's protocol. The LongSAGE libraries were constructed using the I-SAGE long kit (Invitrogen, Carlsbad, Calif.) according to manufacture's instructions. In brief, mRNA was bound to Dyna1 oligo(dT) magnetic beads using the cDNA synthesis module of the kit. Subsequently, mRNA transcripts were converted to cDNA with biotinylated oligo(dT)18 as the primer and Superscript III reverse transcriptase from the cDNA synthesis module of the kit. The cDNA was digested with Nla III, the 3' ends were recovered, the cDNA pool divided in half, and then ligated to LS-adapters 1 and 2. Subsequently, the restriction enzyme, Mme I, was used to release the tags, which were then pooled and ligated to form ditags. Ditags were amplified by PCR and subsequently isolated by polyacrylamide gel electrophoresis (PAGE; 12%) and digested again with Nla III to release the 34 bp Long-SAGE ditags. The ditags were then purified by PAGE (12%). Subsequently, the ditags were concatemerized at their Nla III overhangs with T4 DNA ligase. Concatemers with a minimum size of 500 bp were obtained by gel purification, ligated into the cloning vector pZEro-1 and finally transformed into TOP10 bacteria by electroporation. Sequencing was done by Agencourt (Beverly, Mass.). Additional information about the SAGE and LongSAGE techniques can be found at the Sagenet website.

LongSAGE data were analyzed with SAGE2000 v 4.5 software (www.sagenet.org). Tags corresponding to linker sequences were discarded, and duplicate dimers were counted once only. Both 17 bp LongSAGE tags and corresponding 10 bp SAGE tags were extracted for further analysis. All tags were mapped to their corresponding genes using SAGEmap data from the National Center for Biotechnology Information.

Comparison between the two LongSAGE libraries was carried out with the SAGE2000 software v4.5 (Invitrogen web site). p-values were determined according to Audic S and Claverie J-M (1997) The significance of digital gene expression profiles, *Genome Research* 7:986-995. Tags with multiple matches were excluded. Different tags that matched the same Unigene cluster were combined. A difference with a p-value of <0.05 was considered significant.

GFP$^{high}$ raw Affymetrix chip data files were downloaded from the Rockefeller University database. Microarray Suite (MAS 5.0) software was used to read the raw data and NetAffx annotation file (available on Dec. 10, 2004) was used to annotate the data. Genes marked as present ("P") at least once were used to compare with our LongSAGE data.

Gene Profiling

To determine whether EPI-NCSC represent a novel or a known type of skin-resident stem cell, a neural crest stem cell molecular signature was identified. To do this, gene profiling by long serial analysis of gene expression (LongSAGE) was performed (unpublished results of Y F Hu, Z J Zhang and M Sieber-Blum). Three LongSAGE libraries were prepared and analyzed, with RNA from (1) day 2 EPI-NCSC from anagen hair follicles, (2) embryonic neural crest stem cells (NCSC) at day 2 of culture, and (3) day 7 in vitro differentiated neural crest progeny (NCP) as shown in FIGS. 20(A) and (B).

Figure 20:
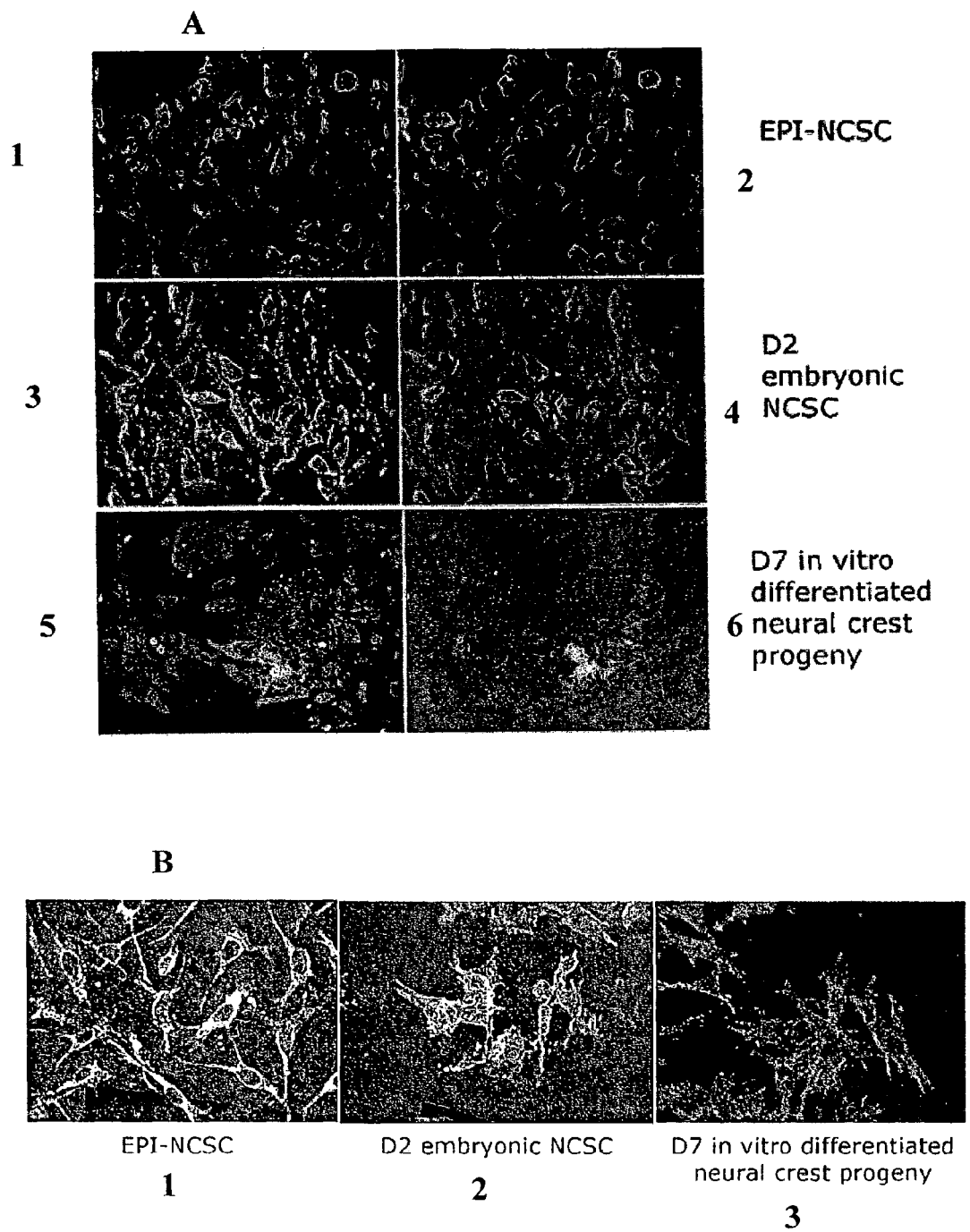
FIG. 20 shows immunocytochemistry validation of two signature genes, identified by Unigene numbers: (A) Mm.1763 (Msx2), wherein the left panel shows fluorescein fluorescence staining and the right panel shows fluorescein fluorescence and DAPI nuclear stain overlay, and (B) Mm.60590 (Myo10) as described herein below.

FIG. 20(A) shows that all day 2 NCSC and EPI-NCSC are intensely immunofluorescent. Most NCSC cells have completely lost expression at day 7 in culture. Also, FIG. 20(B) shows that all day 2 EPI-NCSC and NCSC are intensely immunoreactive. All NCP have significantly down-regulated expression at day 7 in culture. The NCSC library was compared in silico with the NCP library to eliminate house-keeping genes and to identify genes that are expressed at significantly higher levels ($\geq$2-fold; p<0.05) in NCSC than in NCP. A panel of 120 genes was identified. They were then compared with the EPI-NCSC library to identify equivalent abundantly expressed genes (p$\geq$0.07). This comparison yielded a list of 92 non-house-keeping genes that are significantly higher expressed in both embryonic neural crest stem cells and EPI-NCSC compared to in vitro differentiated progeny.

They were then compared to published gene profiling data of bulge-resident epidermal stem cells (keratinocyte stem cells) with whom EPI-NCSC share the niche, and genes common to both epidermal stem cells (keratinocyte stem cells) and EPI-NCSC were eliminated. (See Tumbar T et al. (2004) Defining the epithelial stem cell niche in skin. *Science* 303, 359-363.) This provided a panel of at least 17 genes, which was termed "a neural crest stem cell molecular signature". The neural crest stem cell signature includes the expressed marker genes listed in Table 1. Two signature genes FIG. 20(A), Mm.1763 (Msx2) and Mm.60590 (Myo10), were also analyzed at the protein level by immunocytochemistry (FIG. 20(B)).

Together, the at least 17 molecular signature genes are characteristic of neural crest stem cells, both embryonic (neural tube-derived) and adult (follicular bulge-derived) neural crest stem cells compared to in vitro differentiated progeny, and they are not expressed by bulge-derived epidermal (keratinocyte) stem cells. The molecular signature was compared to published gene profiles of other skin-resident stem cells/progenitors, including facial dermal papilla markers (Fernandes K J L et al. (2004), a dermal niche for multipotent adult skin-derived precursor cells, *Nature Cell Biol.* 6, 1082-1093), a back skin dermal papilla molecular signature [Rendl M et al. (2005) Molecular dissection of mesenchymal-epithelial interactions in the hair follicle. *PloS Biol* 3: e331] and several other follicular cell populations (Rendl M et al., 2005). None of these cell populations expressed the neural crest stem cell molecular signature, confirming the notion that EPI-NCSCs are distinctly different from other types of skin-resident stem cells/progenitors. It is noted that the entire frontal cranial and facial dermis, including the dermal papilla of hair follicles, is of neural crest origin [Le Douarin and Kalcheim, 1999, "The Neural Crest" (eds., Le Douarin and Kalcheim) Cambridge University Press, Cambridge UK, New York, N.Y., 1999].

Despite the neural crest origin of the facial dermis, MNSC cells in the facial dermal papilla expressed high levels of alkaline phosphatase [Fernandes et al (2005; see above)], an enzyme which is not typical for neural crest cells and which was not present in any of our three LongSAGE libraries (unpublished results of Hu Y F, Zhang Z J and Sieber-Blum M). Moreover, the back skin dermal papilla markers Akp2, Alx4, Hoxa9, Zic1, Cntn1 and Enpp1 (Rendl et al., 2005; see above) were not present in any of our three LongSAGE libraries. Importantly, the hematopoietic, adipocyte and epidermal stem cell marker, CD34, was not present in any of our three LongSAGE libraries. From this follows that CD34-positive nestin-expressing cells from the follicular bulge [Amoh Y et al. (2005) Implanted hair follicle stem cells form Schwann cells that support repair of severed peripheral nerves. *PNAS* 102, 17734-17738, and Li L et al. (2003) Nestin expression in hair follicle sheath progenitor cells. *Proc. Natl. Acad Sci. USA* 100, 9958-9961] and EPI-NCSC appear to be distinctly different populations of progenitor cell. Collectively, we conclude that EPI-NCSC are distinctly different from other types of skin-resident stem cell/progenitor.

Up-Scaling of EPI-NCSC Expansion In Vitro

Figure 21:
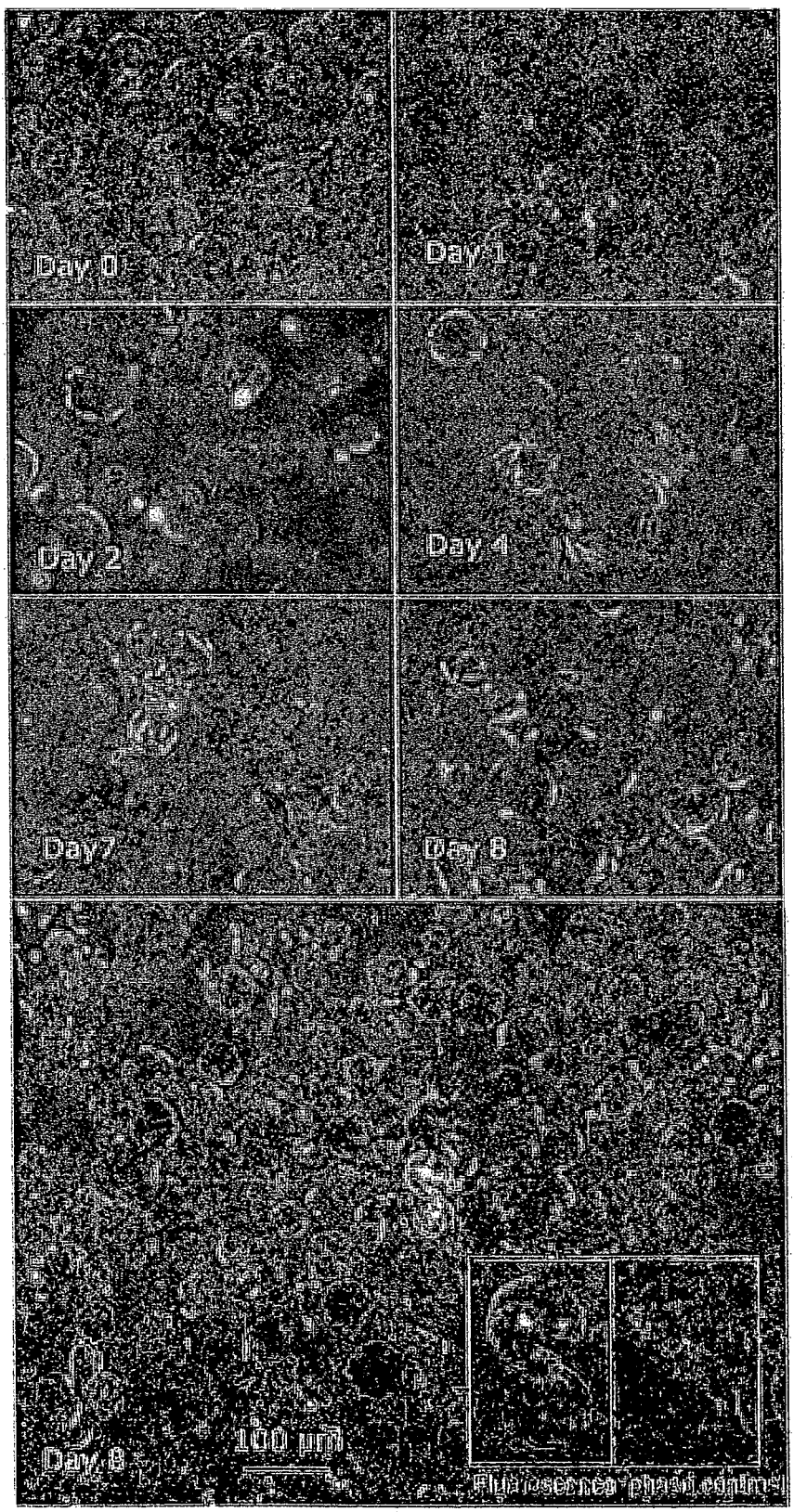
FIG. 21 shows microcarrier sub-culture for cell expansion from day 0 to day 8.

In order to obtain large numbers of EPI-NCSC useful for testing in animal models of human disease, cells from primary explants were grown on fibronectin (50 µg/ml culture medium)-coated collagen microspheres. Cells were grown in primary explants for 3 days after onset of emigration from the bulge explants in Alpha-modified MEM medium supplemented with 5% day 11 chick embryo extract and 10% fetal bovine serum. Medium was then switched to serum-free medium and the cells grown for another two days in primary culture. Cells were then detached with trypsin, and grown on collagen microcarriers (FIG. 21) for 8 days, during the first two days in the absence of serum, and thereafter in the presence of 1% fetal bovine serum. Medium was exchanged every other day. Eight days in microcarrier sub-culture resulted in a 10.9-fold expansion (FIG. 21). The total number of expanded cells obtained per mouse was up to 4.6 million. The number of cells obtained per explant was up to $2.3 \times 10^5$ cells. The data are based on 20 explants, which can be obtained in one preparation from one mouse.

In summary, disclosed herein are methods for producing a substantially pure and expanded population of non-embryonic neural crest stem cells (EPI-NCSCs) from the bulge region of mammalian hair follicles and the population of EPI-NCSCs themselves. EPI-NCSCs from mammals are intriguing for several reasons. First, although, they are post-embryonic in origin, like embryonic neural crest stem cells, EPI-NCSCs have an innate high degree of plasticity. They can give rise to neurons, Schwann cells, smooth muscle cells, chondrocytes, melanocytes and possibly other cell types. Second, they are abundant and easily accessible. Thus, EPI-NCSCs are attractive candidates for diverse cell therapy applications. Since they are located in an accessible tissue, invasive surgery will not be necessary to harvest them. Furthermore, since they can be obtained from the living organism, they are good candidates for autologous transplantation, which will avoid rejection of the transplant.

While the present invention has now been described and exemplified with some specificity, those skilled in the art will appreciate the various modifications, including variations, additions, and omissions that may be made in what has been described. Accordingly, it is intended that these modifications also be encompassed by the present invention and that the scope of the present invention be limited solely by the broadest interpretation that lawfully can be accorded the appended claims.

PUBLICATIONS

Alexanian A R and Sieber-Blum M. 2003. Differentiating adult hippocampal stem cells into neural crest derivatives. Neuroscience. 118: 1-5.

Baroffio, A., Dupin, E. and Le Douarin, N. M. 1988. Clone-forming ability and differentiation potential of migratory neural crest cells. Proc. Natl. Acad. Sci. USA 85: 5325-5329.

Baumann K I, Chan E, Halata Z, Senok S S and Yung W H. 1996. An isolated rat vibrissal preparation with stable responses of slowly adapting mechanoreceptors. Neurosci. Lett. 26: 1-4.

Bixby S, Kruger G M, Mosher J T, Joseph N M, Morrison S J. 2002. Cell-intrinsic differences between stem cells from different regions of the peripheral nervous system regulate the generation of neural diversity. Neuron 35: 643-656.

Bronner-Fraser, M. and Fraser, S. E. 1988. Cell lineage analysis reveals multipotency of some avian neural crest cells. Nature 335: 161-164.

Chai, Y., Jiang, X., Ito, Y., Bringas, P., Jr., Han, J., Rowitch, D. H., Soriano, P., McMahon, A. P. and Sucov, H. M. 2000. Fate of the mammalian cranial neural crest during tooth and mandibular morphogenesis. Development 127, 1671-1679.

Danielian, P. S., Muccino, D., Rowitch, D. H., Michael, S. K. and McMahon, A. P. (1998). Modification of gene activity in mouse embryos in utero by a tamoxifen-inducible form of Cre recombinase. Curr. Biol. 8, 1323-1326.

Davis, C. A., Noble-Topham, S. E., Rossant, J. and Joyner, A. L. 1988. Expression of the homeo box-containing gene En-2 delineates a specific region of the developing mouse brain. Genes Dev. 2: 361-371.

Duff, R. S., Langtimm, C. J., Richardson, M. K. and Sieber-Blum, M. 1991. In vitro clonal analysis of progenitor cell patterns in dorsal root and sympathetic ganglia of the quail embryo. Dev. Biol. 147: 451-459.

Echelard, Y., Vassileva, G. and McMahon, A. P. 1994. Cis-acting regulatory sequences governing Wnt1 expression in the developing mouse CNS. Development 120: 2213-2224.

Friedrich, G. and Soriano, P. 1991. Promoter traps in embryonic stem cells: a genetic screen to identify and mutate developmental genes in mice. Genes. Dev. 5: 1513-1523.

Fuchs, E., Merrill, B. J., Jamora, C. and DasGupta, R. 2001. At the roots of a never-ending cycle. Dev. Cell. 1: 13-25.

Galileo S A, Gray G E, Owens G C, Majors J and Sanes J R 1990. Neurons and glia arise from a common progenitor in chicken optic tectum: Demonstration with two retroviruses and cell type-specific antibodies. Proc. Natl. Acad. Sci. USA 87: 458-462.

Gershon, M. D., Chalazonitis, A. and Rothman, T. P. 1993. From neural crest to bowel: development of the enteric nervous system. J. Neurobiol. 24: 199-214.

Henion, P. D. and Weston, J. A. 1997. Timing and pattern of cell fate restrictions in the neural crest lineage. Development 124: 4351-4659.

Ito, K. and Takeuchi, T. 1984. The differentiation in vitro of the neural crest cells of the mouse embryos. J. Embryol. Exp. Morphol. 84: 49-62.

Ito, K., Morita, T. and Sieber-Blum, M. 1993. In vitro clonal analysis of mouse neural crest development. Dev. Biol. 157: 517-525.

Ito K and Sieber-Blum M. 1993. Pluripotent and developmentally restricted neural crest-derived cells in posterior visceral arches. Dev. Biol. 156: 191-200.

Jiang, X., Iseki, S., Maxson, R. E., Sucov, H. M. and Morriss-Kay, G. M. 2002. Tissue origins and interactions in the mammalian skull vault. Dev. Biol. 241: 106-116.

Josephson R, Müller T, Pickel J, Okabe S, Reynolds K, Turner P A, Zimmer A and McKay R D G. 1998. POU transcription factors control expression of CNS stem cell-specific genes. Development 125: 3087-3100.

Kobayashi K, Rochat A, Barrandon Y. 1993. Segregation of keratinocyte colony-forming cells in the bulge of the rat vibrissa. Proc. Natl. Acad. Sci. USA 90: 7391-7395.

Kruger G M, Mosher J T, Bixby S, Joseph N, Iwashita T, Morrison S J. 2002. Neural crest stem cells persist in the adult gut but undergo changes in self-renewal, neuronal subtype potential, and factor responsiveness. Neuron 35: 657-669.

Kuhlbrodt K, Herbarth B, Sock E, Hermans-Borgmeyer I, Wegner M. 1998. Sox10, a novel transcription modulator in glial cells. J. Neurosci. 18: 237-250.

Kypriotou M, Fossard-Demoor M, Chadjichristos C, ghayor C, de Crombrugghe B, Pujol J P and Galera P (2003). SOX9 exerts a bifunctional effect on type II collagen (COL2A1) expression in chondrocytes depending on the differentiation state. DNA Cell Biol. 22, 119-129.

Le Douarin N. M. and Kalcheim, C. 1999, In The Neural Crest (eds. Le Douarin, N. M. and Kalcheim, C.). Cambridge University Press, Cambridge, U.K., New York, N.Y.

Lee, M. K., Rebhun, L. I. and Frankfurter A. 1990. Posttranslational modification of class III beta-tubulin. Pro. Natl. Acad. Sci. USA 87: 7195-7199.

Lendahl U, Zimmerman L B and McKay R D. 1990. CNS stem cells express a new class of intermediate filament protein. Cell 60: 585-595.

Li, L, Mignone J, Yang M, Matic M, Pernma S, Enikolopov G, Hoffman R M. 2003. Nestin expression in hair follicle sheath progenitor cells. Proc. Natl. Acad. Sci. USA 100: 9958-9961.

Lothian C and Lendahl U. 1997. An evolutionarily conserved region in the second intron of the human nestin gene directs gene expression to CNS progenitor cells and to early neural crest cells. Eur. J. Neurosci 9: 452-462.

McMahon, A. P., Joyner, A. L., Braddley, A., and McMahon, J. A. 1992. The midbrain-hindbrain phenotype of Wnt1−/

Wnt1⁻ mice results from stepwise deletion of engrailed-expressing cells by 9.5 days post-coitum. Cell 69: 581-595.

Millar, S. E., Willert, K., Salinas, P. C., Roelink, H., Nusse, R., Sussman, D. J. and Barsh, G. S. 1999. WNT signaling in the control of hair growth and structure. Dev. Biol. 207: 133-149.

Molven, A., Njolstad, P. R. and Fjose, A. 1991. Genomic structure and restricted neural expression of the zebrafish Wnt1 (int-1) gene. EMBO J. 10: 799-807.

Mori-Akiyama Y, Akiyama H, Rowitch D H and de Crombrugghe B (2003). Sox9 is required for determination of the chondrogenic cell lineage in the cranial neural crest. PNAS 100, 9360-9365.

Mujtaba T, Mayer-Proschel M and Rao M S. 1998. A common neural progenitor for the CNS and PNS. Dev. Biol. 200:1-15.

Nataf, V., Mercier, P., Ziller, C., Le Douarin, N. M., 1993. Novel markers of melanocyte differentiation in the avian embryo. Exp. Cell Res. 207: 171-182.

Nishimura E. K., Jordan S. A, Oshima H., Yoshida H, Osawa M, Moriyama M, Jackson J., Barrandon Y., Miyachi Y. and Nishikawa S.-I. 2002. Dominant role of the niche in melanocyte stem-cell fate determination. Nature 416, 854-860.

Oshima H, Rochat A, Kedzia C, Kobayashi K, Barrandon Y. 2001. Morphogenesis and renewal of hair follicles from adult multipotent stem cells. Cell 104: 233-245.

Parkinson D B, Dong Z, Bunting H, Whitfield J, Meier C, Marie H, Mirsky R & Jessen K R. 2001. Transforming growth factor beta (TGFbeta) mediates Schwann cell death in vitro and in vivo: examination of c-Jun activation, interactions with survival signals, and the relationship of TGF-beta-mediated death to Schwann cell differentiation. J Neurosci. 21: 8572-85.

Peters E M J, Tobin D J, Botchkareva N, Maurer M and Paus R. 2002. Migration of melanoblasts into the developing murine hair follicle is accompanied by transient c-kit expression. J. Histochem. Cytochem. 50: 751-766.

Reddy, S., Andl, T., Bagasara, A., Lu, M. M., Epstein, D. J., Morrisey, E. E. and Millar, S. E. 2001. Characterization of Wnt gene expression in developing and postnatal hair follicles and identification of Wnt5a as a target of Sonic hedgehog in hair follicle morphogenesis. Mech. Dev. 107: 69-82.

Rehberg S, Lischka P, Glaser, G, Stamminger T, Wegner M, and Rosorius O. 2002. Sox10 in an active nucleocytoplasmatic shuttle protein, and shuttling is crucial for Sox10-mediated transactivation. Mol. and Cell. Biol. 22: 5826-5834.

Richardson, M. K. and Sieber-Blum, M. 1993. Pluripotent neural crest cells in the developing skin of the quail embryo. Dev. Biol. 157: 348-358.

Rico, B., Xu, B. and Reichardt, L. F. 2002. TrkB receptor signaling is required for establishment of GABAergic synapses in the cerebellum. Nat. Neurosci. 5: 225-233.

Shah N M, Marchionni M A, Isaacs I, Stroobant O and Anderson D J. 1994. Glial growth factor restricts mammalian neural crest stem cells to a glial fate. Cell 77, 349-360.

Sieber-Blum, M. In: The neural crest colony assay: assessing molecular influences on development in culture. In: The Neuron in Tissue Culture (L. W. Haynes, ed.) IBRO, John Wiley & Sons Ltd. (1999) pp. 5-22.

Sieber-Blum, M. 1989. Commitment of neural crest cells to the sensory neuron lineage. Science 243: 1608-1611.

Sieber-Blum, M. and Sieber, F. 1984. Heterogeneity among early quail neural crest cells. Brain. Res. 316: 241-246.

Sieber-Blum, M. and Cohen, A. M. 1980. Clonal analysis of quail neural crest cells: they are pluripotent and differentiate in vitro in the absence of noncrest cells. Dev. Biol. 80: 96-106.

Sieber-Blum M, Szeder V, Grim M and Halata Z. 2003. Mammalian Merkel cells are neural crest derivatives. In: "The Merkel Cell; Structure-Development-Function-Cancerogenesis". K. I. Baumann, Z. Halata and I. Moll (eds). Springer, Berlin.

Soriano, P. 1999. Generalized lacZ expression with the ROSA26 Cre reporter strain. Nat. Genet. 21: 70-71.

Stemple, D. L., Mahanthappa, N. K. and Anderson, D. J. 1988. Basic FGF induces neuronal differentiation, cell division, and NGF dependence in chromaffin cells: a sequence of events in sympathetic development. Neuron 1: 517-525.

St-Jacques, B., Dassule, H. R., Karavanova, I., Botchkarev, V. A., Li, J., Danielian, P. S., McMahon, J. A., Lewis, P. M., Paus, R. and McMahon, A. P. 1998. Sonic hedgehog signaling is essential for hair development. Curr. Biol. 8: 1058-1068.

Szeder, V., Grim, M., Halata, Z., and Sieber-Blum, M. 2003. Neural crest origin of mammalian Merkel cells. Dev. Biol. 253: 258-263.

Toma J G, Akhavan M, Fernandez K J L, Barnabé-Heider F, Sadikot A, Kaplan D R and Miller F D. 2001. Isolation of multipotent adult stem cells from the dermis of mammalian skin. Nature Cell Biol. 3: 778-784.

Toma J G, McKenzie I A, Bagli D, Miller F D (2005) Isolation and characterization of multipotent skin-derived precursors from human skin. Stem Cells 23:727-37.

Wilkinson, D. G., Bailes, J. A., Champion, J. F. and McMahon, A. P. 1987. Expression of the proto-oncogene int-1 is restricted to specific neural cells in the developing mouse embryo. Cell 50: 79-88.

Wolda, S. L., Moody, C. J., and Moon, R. T. 1993. Overlapping expression of Xwnt-3A and XWnt1 in neural tissue of *Xenopus laevis* embryos. Dev. Biol. 155: 46-57.

Zehentner B K, Haussmann A and Burtscher H (2002). The bone morphogenetic protein antagonist Noggin is regulated by Sox9 during endochondral differentiation. Develop. Growth Differ. 44, 1-9.

Zorick T S, Syroid D E, Arroyo E, Scherer S S, Lemke G. 1996. The transcription factors SCIP and Krox-20 mark distinct stages and cell fates in Schwann cell differentiation. Mol. Cell. Neurosci. 8: 129-145.

We claim:

1. A method of producing an isolated population of primate multipotent non-embryonic epidermal neural crest stem cells from hair follicles, the method comprising the steps of:
   (a) providing epidermal tissue with hair follicles from a primate;
   (b) dissecting the hair follicles by removing dermis, dermal papilla, connective tissue and fat cells to isolate the bulge region of the hair follicles, wherein the bulge region is the source of epidermal neural crest stem cells (EPI-NCSC);
   (c) culturing the bulge regions as adherent explants on collagen-, and fibronectin-coated culture substrates to isolate the non-embryonic epidermal neural crest stem cells; and
   (d) culturing the isolated EPI-NCSCs as adherent cells under conditions to produce the population of non-embryonic neural crest stem cells, wherein the cells (i) have a purity level of greater than 70% EPI-NCSCs, (ii) are capable of undergoing differentiation to give rise to neural crest cell derivatives, (iii) are highly proliferative in cell culture, (iv) are highly motile, (v) exhibit a high degree of plasticity, (vi) are stellate shape in morphology and (vii) are characterized by the positive expression of Sox-10 and Nestin.

2. The method of claim 1 further comprising the step of:
   (e) expanding the isolated neural crest cell population of step as adherent cells by sub-culture.

3. The method of claim 1 wherein the culture of step (d) includes the following components: collagen, fibronectin, alpha-modified MEM culture medium, insulin, transferrin, selenium, at least three essential fatty acids, day 11 chick embryo extract and growth factors, such as fibroblast growth factors, epidermal growth factors and neurotrophins.

4. The method of claim 1 wherein the isolation of the neural crest stem cells from primate hair follicles yields at least $2.2 \times 10^3$ cells per explant, within 3 to 4 days after the onset of emigration in primary explant culture.

5. The method of claim 1 wherein the isolated primate multipotent cell population is further characterized by the positive expression of marker genes including Pcbp4 (Mm.286394), Msx2 (Mm.1763), H1fx (Mm.33796), Thop1 (Mm.26995), Vars2 (Mm.28420), Myo10 (Mm.60590), 2700094K13Rik (Mm.259293), Ets1 (Mm.292415), Pygo2 (Mm.22521) Adam12 (Mm.323601) 5730449L18Rik (Mm.21065), Rex3 (Mm.14768), Vdac1 (Mm.3555), AU041707 (Mm.200898), Crmp1 (Mm.290995), Ube4b (Mm.288924) and combinations thereof.

6. The method of claim 1 wherein the cell population has a purity level of at least 83% EPI-NCSCs without any need to further purify the EPI-NCSCs.

7. The method of claim 1 wherein the isolated primate multipotent cells are capable of differentiating into cranial neural crest cells derivatives including neurons, Schwann cells, smooth muscle cells, chondrocytes and melanocytes.

8. The method of claim 1 wherein the cells are adherent cells in that they adhere to a substratum comprised of collagen and fibronectin.

9. The population of claim 1 wherein the cells are human cells.

10. The population of claim 1 wherein the cells are adult, juvenile or newborn cells.

11. An isolated population of multipotent primate non-embryonic neural crest stem cells obtained from the epidermal bulge region of a hair follicle, wherein the population (i) has a purity level of greater than 70% epidermal neural crest stem cells, (ii) is capable of undergoing differentiation to give rise to neural crest cell derivatives, (iii) is highly proliferative in cell culture, (iv) is highly motile, (v) exhibits a high degree of plasticity, (vi) is stellate shaped in morphology, and (vii) is characterized by the positive expression of Sox-10 and Nestin.

12. The population of claim 11 wherein the population is composed of greater than 83% epidermal neural crest stem cells at the onset of emigration from the hair follicle without any need to further purify the cells.

13. The population of claim 11 wherein the cells are human cells.

14. The population of claim 11 wherein the cells are adult, juvenile or newborn cells.

15. The population of claim 11 wherein the neural crest cell derivatives comprise neurons, Schwann cells, smooth muscle cells, chondrocytes and melanocytes.

16. The population of claim 11 wherein the neural crest stem cells are further characterized by the positive expression of marker genes including Pcbp4 (Mm.286394), Msx2 (Mm.1763), H1fx (Mm.33796), Thop1 (Mm.26995), Vars2 (Mm.28420), Myo10 (Mm.60590), 2700094K13Rik (Mm.259293), Ets1 (Mm.292415), Pygo2 (Mm.22521) Adam12 (Mm.323601) 5730449L18Rik (Mm.21065), Rex3 (Mm.14768), Vdac1 (Mm.3555), AU041707 (Mm.200898), Crmp1 (Mm.290995), Ube4b (Mm.288924) and combinations thereof.

* * * * *

UNITED STATES PATENT AND TRADEMARK OFFICE
CERTIFICATE OF CORRECTION

| | | |
|---|---|---|
| PATENT NO. | : 8,030,072 B2 | Page 1 of 1 |
| APPLICATION NO. | : 11/376498 | |
| DATED | : October 4, 2011 | |
| INVENTOR(S) | : Maya Sieber-Blum et al. | |

It is certified that error appears in the above-identified patent and that said Letters Patent is hereby corrected as shown below:

Please replace Claims 2 and 7 as follows:

Column 30, line 59, Claim 2:
--The method of Claim 1 further comprising the step of: (e) expanding the isolated neural crest cell population of step (d) as adherent cells by sub-culture.--

Column 31, line 19, Claim 7:
--The method of claim 1 wherein the isolated primate multipotent cells are capable of differentiating into cranial neural crest cell derivatives including neurons, Schwann cells, smooth muscle cells, chondrocytes and melanocytes.--

Signed and Sealed this
Seventh Day of August, 2012

David J. Kappos
*Director of the United States Patent and Trademark Office*

SEQUENCE LISTING

<160> NUMBER OF SEQ ID NOS: 12

<210> SEQ ID NO 1
<211> LENGTH: 26
<212> TYPE: DNA
<213> ORGANISM: Artificial

```
<220> FEATURE:
<223> OTHER INFORMATION: Synthetic PCR primer

<400> SEQUENCE: 1
actatgccaa gggacaacct tacatc                                          26

<210> SEQ ID NO 2
<211> LENGTH: 24
<212> TYPE: DNA
<213> ORGANISM: Artificial
<220> FEATURE:
<223> OTHER INFORMATION: Synthetic PCR primer

<400> SEQUENCE: 2
acatagagcg tgacctgaga ggtc                                            24

<210> SEQ ID NO 3
<211> LENGTH: 18
<212> TYPE: DNA
<213> ORGANISM: Artificial
<220> FEATURE:
<223> OTHER INFORMATION: Synthetic PCR primer

<400> SEQUENCE: 3
ggcccaagct aaagttgg                                                   18

<210> SEQ ID NO 4
<211> LENGTH: 19
<212> TYPE: DNA
<213> ORGANISM: Artificial
<220> FEATURE:
<223> OTHER INFORMATION: Synthetic PCR primer

<400> SEQUENCE: 4
caagccagac ctcacagcg                                                  19

<210> SEQ ID NO 5
<211> LENGTH: 18
<212> TYPE: DNA
<213> ORGANISM: Artificial
<220> FEATURE:
<223> OTHER INFORMATION: Synthetic PCR primer

<400> SEQUENCE: 5
cccgtgggct caaaatgt                                                   18

<210> SEQ ID NO 6
<211> LENGTH: 19
<212> TYPE: DNA
<213> ORGANISM: Artificial
<220> FEATURE:
<223> OTHER INFORMATION: Synthetic PCR primer

<400> SEQUENCE: 6
tgggggcagt gtcagtagc                                                  19

<210> SEQ ID NO 7
<211> LENGTH: 19
<212> TYPE: DNA
<213> ORGANISM: Artificial
<220> FEATURE:
<223> OTHER INFORMATION: Synthetic PCR primer

<400> SEQUENCE: 7
aagaacatgt gcaagctca                                                  19
```

-continued

```
<210> SEQ ID NO 8
<211> LENGTH: 20
<212> TYPE: DNA
<213> ORGANISM: Artificial
<220> FEATURE:
<223> OTHER INFORMATION: Synthetic PCR primer

<400> SEQUENCE: 8
acaacaaaaa gagtccaggc                                                   20

<210> SEQ ID NO 9
<211> LENGTH: 19
<212> TYPE: DNA
<213> ORGANISM: Artificial
<220> FEATURE:
<223> OTHER INFORMATION: Synthetic PCR primer

<400> SEQUENCE: 9
caagccagac ctcacagcg                                                    19

<210> SEQ ID NO 10
<211> LENGTH: 20
<212> TYPE: DNA
<213> ORGANISM: Artificial
<220> FEATURE:
<223> OTHER INFORMATION: Synthetic PCR primer

<400> SEQUENCE: 10
ggtgtccagg ctggtttctc                                                   20

<210> SEQ ID NO 11
<211> LENGTH: 20
<212> TYPE: DNA
<213> ORGANISM: Artificial
<220> FEATURE:
<223> OTHER INFORMATION: Synthetic PCR primer

<400> SEQUENCE: 11
acagctgaag gaagagatgg                                                   20

<210> SEQ ID NO 12
<211> LENGTH: 20
<212> TYPE: DNA
<213> ORGANISM: Artificial
<220> FEATURE:
<223> OTHER INFORMATION: Synthetic PCR primer

<400> SEQUENCE: 12
gatttgctgt cctgggtatc                                                   20
```